United States Patent
Christmas et al.

(10) Patent No.: US 6,210,329 B1
(45) Date of Patent: Apr. 3, 2001

(54) APPARATUS FOR ORGANIZING, TRANSPORTING, AND FACILITATING THE USE OF OBSTETRICAL AND OTHER MEDICAL DEVICES AND SUPPLIES

(75) Inventors: Robert Caldwell Christmas, Marietta, GA (US); Robert Watts, Malvern, PA (US)

(73) Assignee: Docsystems, Inc., Malvern, PA (US)

( * ) Notice: Subject to any disclaimer, the term of this patent is extended or adjusted under 35 U.S.C. 154(b) by 0 days.

(21) Appl. No.: 09/370,720

(22) Filed: Aug. 9, 1999

(51) Int. Cl.[7] ................... A61B 8/00; A61B 8/12
(52) U.S. Cl. ............................. 600/437; 600/459
(58) Field of Search ...................... 600/437, 459, 600/446; 312/209; 206/369, 379, 534, 538, 828; 52/27; 128/200.23; 5/503.1; 219/202, 521, 387

(56) References Cited

U.S. PATENT DOCUMENTS

| | | | |
|---|---|---|---|
| 3,082,050 | 12/1960 | Baxter et al. | 312/209 |
| 3,732,955 | 5/1973 | Carter et al. | 190/51 |
| 3,743,372 | 7/1973 | Ruggerone | 312/108 |
| 4,194,628 | 3/1980 | Campos | 206/570 |
| 4,413,629 | 11/1983 | Durley, III | 128/660 |
| 4,448,307 * | 5/1984 | Roggenkemp | 206/369 |
| 4,523,078 | 6/1985 | Lehmann | 219/202 |
| 4,796,790 | 1/1989 | Hamilton | 224/253 |
| 5,107,636 * | 4/1992 | Schindele et al. | 52/27 |
| 5,183,994 | 2/1993 | Bowles, Sr. et al. | 219/387 |
| 5,397,875 | 3/1995 | Bechtold, Jr. | 219/521 |
| 5,447,237 | 9/1995 | Carter et al. | 206/570 |
| 5,651,152 * | 7/1997 | Ritchie et al. | 5/503.1 |
| 5,687,063 | 11/1997 | Chabert | 361/726 |
| 5,833,330 * | 11/1998 | Kos | 312/209 |
| 5,941,241 * | 8/1999 | Weinstein et al. | 128/200.23 |

FOREIGN PATENT DOCUMENTS

| | | |
|---|---|---|
| 1 541 243 | 1/1970 | (DE) . |
| 2 627 977 | 9/1989 | (FR) ................... A61B/8/00 |
| WO 98/05257 | 2/1998 | (WO) ................. A61B/7/02 |

* cited by examiner

Primary Examiner—Marvin M. Lateef
Assistant Examiner—Ali M. Imam
(74) Attorney, Agent, or Firm—Bernstein & Associates; Jason A. Bernstein; John W. Greenwald

(57) ABSTRACT

An apparatus for organizing, transporting, and using medical devices and supplies during obstetrical evaluations, comprising a portable housing with an alarm system for contents thereof, a base housing capable of being structurally and electrically coupled to by the portable housing and optional housings, and a fixture mounting bracket for attaching the base housing to an examination table. The portable housing and base housing preferably have compartments for medical devices and supplies. The portable housing has a medical device compartment for accepting a Doppler receiving insert for storing a conventional Doppler device with a probe connected to a base, for accepting a customized Doppler base unit of an integral Doppler device with a probe connected to the base, or for accepting a scanhead receiving insert for storing a sonogram device with a scanhead connected to a console. The portable housing preferably also has a gel bottle compartment with a gel bottle heater for maintaing the temperature of a gel bottle stored therein. The alarm system preferably has at least one trigger device in the medical device compartment. Optional housings may include a recording housing for use with the Doppler or sonogram devices and/or a blood pressure housing. The base housing is attached to an examination table with the portable housing coupled thereto and conveniently located for use with a patient on the table with the medical devices secured and protected therein, and the portable housing may then be decoupled from the base housing for transport to other places.

58 Claims, 14 Drawing Sheets

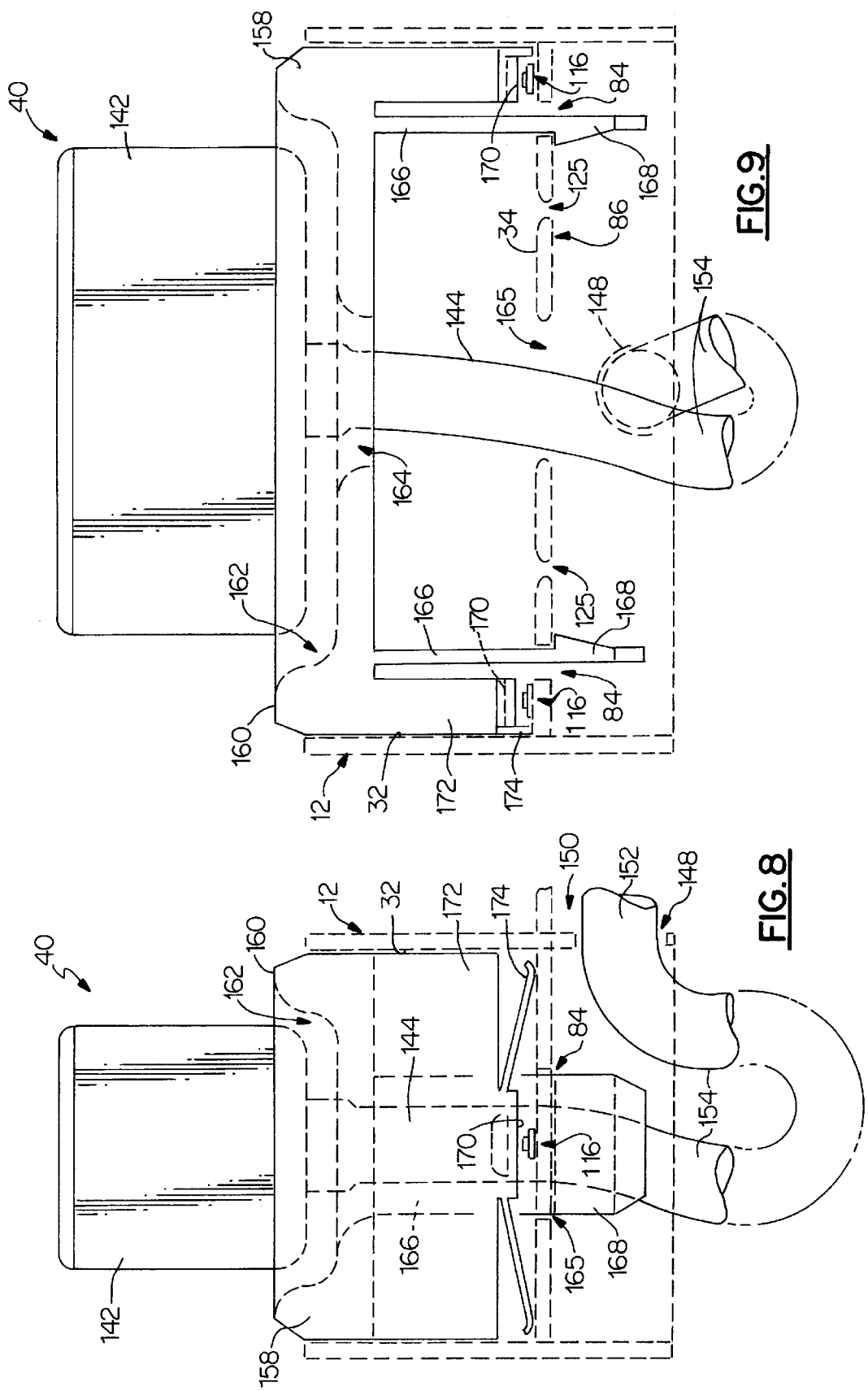

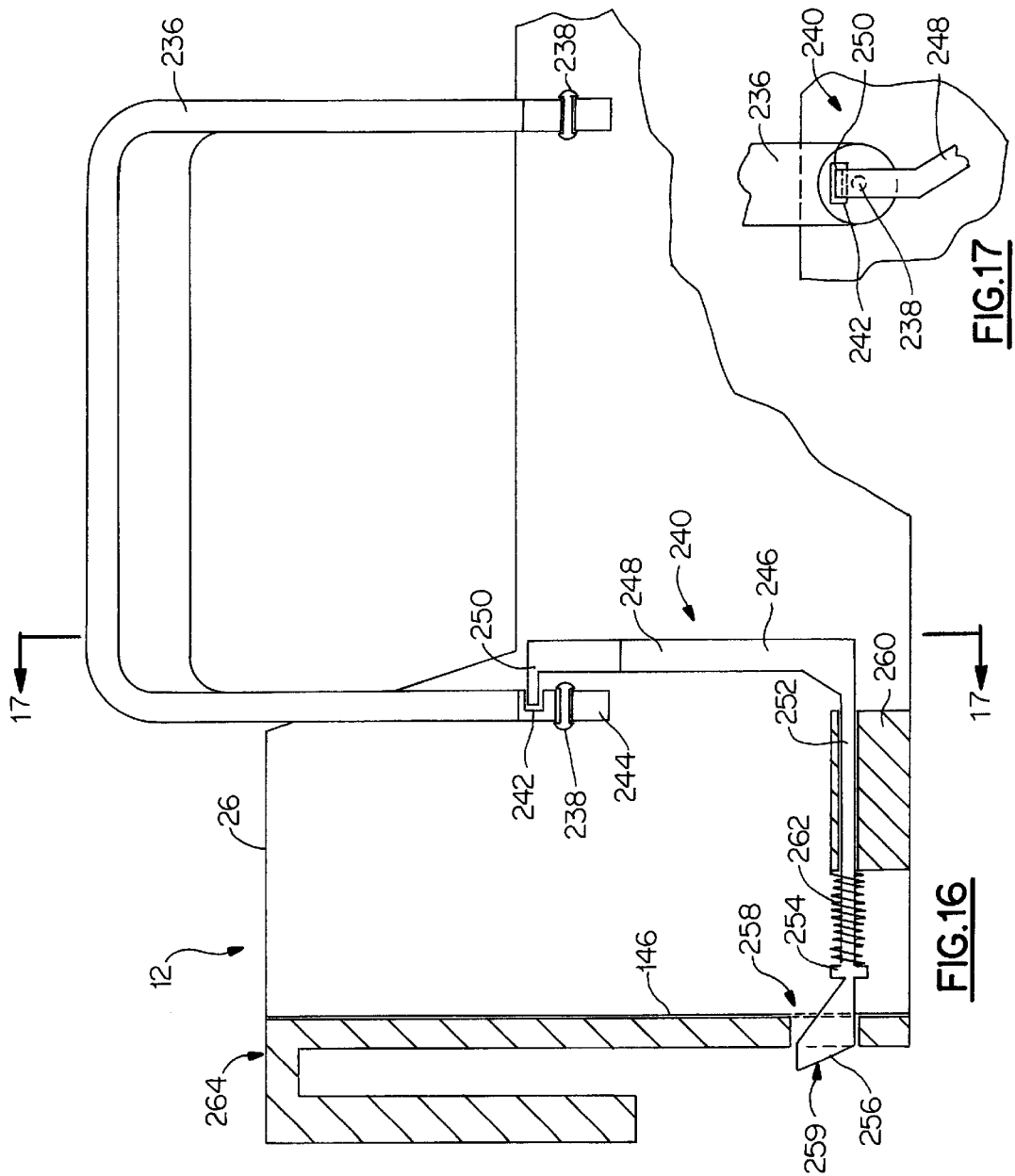

APPARATUS FOR ORGANIZING, TRANSPORTING, AND FACILITATING THE USE OF OBSTETRICAL AND OTHER MEDICAL DEVICES AND SUPPLIES

FIELD OF THE INVENTION

The present invention relates to medical storage and carrying cases, and more particularly, to an apparatus for organizing, storing, transporting and utilizing devices and supplies commonly used for obstetrical or vascular surgical and postoperative evaluations.

BACKGROUND OF THE INVENTION

Most obstetricians and nurse-midwives recommend that the first prenatal medical appointment for a pregnant woman be scheduled as early as possible in the pregnancy. Typically, subsequent prenatal visits initially occur at one-month intervals, then twice a month, then weekly in the latter stages of uncomplicated pregnancy. Complicated pregnancies may warrant twenty or more prenatal visits. For many practices of obstetrics-gynecology, prenatal visits constitute the majority of office appointments. Each prenatal visit recurrently utilizes a small collection of obstetrical supplies and instruments.

At each prenatal visit the practitioner attempts to detect, across the surface of the maternal abdominal wall, evidences of fetal cardiac activity. Traditionally this was ascertained by auscultation of fetal heart sounds using a specialized obstetrical stethoscope. Contemporary methods are more rapid and reliable, and typically give the gravid patient the immediate reassurance that her developing baby is alive and well. Of such newer cardiac activity detection methods, sensitive microphones and fetal electrocardiogram recordings have been largely supplanted in today's medical office by the compact, easy-to-use ultrasonic Doppler device. Essentially a medical sonar, it detects Doppler frequency shifts in those returning ultrasonic energy waves which it has reflected off moving components of the fetal cardiovascular system, such as flow of blood in the largest fetal vessels. Such frequency shifts are then converted to an audible signal.

Most commercially available Doppler units are portable, battery-operated devices small enough to be cradled in the palm of the hand. These typically comprise a probe or transducer that is applied to the surface of the maternal abdomen and wired to a separate speaker-containing base unit. When the device is not in use it may be placed in the lab coat pocket of the practitioner, or left on or within storage cabinetry. Some models provide a clip by which the base unit may be attached to the practitioner's pocket edge or belt, and some provide a niche within the base unit, to store the probe.

A hand-held fetal Doppler is an expensive medical device. It is fragile, small enough to be easily concealed, and fascinates the patient and her family with its function: they are able by means of it to hear sounds made, albeit indirectly, by the baby. To a young child accompanying its mother into the examination room, the device may resemble a toy. Perhaps because of its capabilities and natural appeal, dropping, tampering and theft are the chief reasons for Doppler repair or replacement. Therefore the hand-held Doppler, while it must be easily accessible to medical personnel, needs protection from unauthorized handling. This might involve fixing the Doppler to a protective base, integrating the Doppler function into a multifunctional piece of equipment too large to be concealed, and/or fashioning an alarm system triggered by tampering.

Practical advances in hand-held Doppler design generally comprise elimination of the wire or cord between the Doppler probe and base unit, digital display of the fetal heart rate, and multiple probes for a single base unit.

Doppler devices minus the wire or cord avoid the annoyances of entanglement, twisting, or inappropriate wire length that can interfere with Doppler use. One such design integrates a transmitter into the Doppler probe. It sends an RF or infrared signal to a remote base unit where a circuit converts the signal into a sound. Another design simply integrates speaker and probe into a single hand-held housing. Accordingly, the present invention accommodates such variations in Doppler design, and additionally provides mechanisms for theft and tampering protection for Doppler models with either one or two portable housings.

Models which numerically display fetal heart rate obviate the need for the practitioner to count the fetal signal over a short time span and then mentally convert the data to beats per minute. However, the base unit must be positioned by the present invention so that the practitioner can easily read the fetal heart rate display.

Doppler models with more than one probe allow the practitioner to select the frequency range of ultrasonic wave detection that is most appropriate for the particular gestational age of the fetus. This enables, for example, Doppler detection of fetal life earlier in pregnancy or in obese patients. Protected storage of a readily accessible standby probe is therefore preferable, and is not provided by the prior art.

As with Doppler, sonography (ultrasound scanning) involves the painless application of a small hand-held device, the sonogram scanhead, upon a body surface, in this case the maternal abdominal or vaginal wall, enhanced by ultrasound conduction gel applied at the interface. This technology converts the reflected ultrasonic energy waves into cross-sectional fixed or moving images of the targeted internal wave-reflecting structures. Laypersons and professionals alike regard it as the chief diagnostic technique for many obstetric situations. Its understandable, instantaneous images enable the skilled medical professional to demonstrate findings to the patient as her scan progresses. Such participation of the patient demystifies the obstetric complication and often communicates the rationale for the medical recommendations which follow.

Not uncommonly at a routine prenatal visit a practitioner must broach the disturbing possibility of an obstetric problem amenable to ultrasound study. A sonogram offered immediately, not scheduled for some more convenient day, minimizes the patient's understandable tension and suspense and allows prompt redirection of medical management. Unfortunately, however, the scanning equipment often lies idle and inaccessible in an examination room then occupied by another patient. Scan capability in each exam room should instead permit an immediate sonogram with minimal disruption of office function.

While sonography should hardly be offered primarily to entertain, it is immensely popular with patients and it lacks known medical risk. Because it can reveal the undeniably humanoid image and heart motions of the fetus several weeks before the hand-held Doppler can demonstrate fetal life, sonography can foster that earlier parent-to-child and parent-to-parent bonding and commitment which invariably strengthen the family unit and promote a desire to nurture the pre-born child. Sensing this, even couples with apparently uncomplicated pregnancies desire and benefit from a sonogram.

Whether because of client expectations or the weight of proven medical benefit, ready availability of scan equipment in each obstetrical exam room is highly desirable. While someday sonography may supplant Doppler fetal heart detection at the routine prenatal visit, today the low portability and high cost of scanning equipment restricts any-visit sonography to the offices of perinatologists and a very few generalist obstetricians. The practical need for hand-portable, sophisticated yet cost-effective obstetric sonography equipment remains unmet. Miniaturization of already costly sonography devices may render them too expensive for the office. Situating a complete conventional scanning unit in each exam room, likewise unaffordable (such computer-based devices suffer rapid obsolescence), additionally encourages tampering with the unattended equipment.

The conventional sonogram scanhead itself is as compact as is a hand-held Doppler. Its attached two-meter computer style electronic cable with multi-pin connector yields this scanhead assembly somewhat more awkward than a hand-held Doppler to transport. Yet if it were possible to scan a patient in any exam room by carrying a single scanhead assembly room to room, each time recruiting the function of a single remotely placed signal processing console, portability might be achieved without costly miniaturization. The current invention accomplishes a portability system by which such a scanhead assembly could be easily and securely carried from room to room.

There are several design preferences for such a portability system. The scanhead assembly of most commercial sonogram devices is preferably accommodated within a portable housing which protects it, and allows for its convenient use and transfer. The practitioner should find it convenient to accurately engage and gently disengage the pin-socket arrays of the necessary electrical connectors. The system should provide dedicated routes for the electronic cables that connect scanhead to central processing console. At each scanning location, the position of the scanhead-bearing portable housing should not compromise the excursion of the scanhead to any body site typically scanned during pregnancy.

The present invention furthers the quest for portable office sonography. Design and installation of sonography equipment to be used with the present invention may be based on and/or coordinated with the design of the invention as discussed hereinbelow. Such accommodation is contemplated by and intended to be within the scope of the invention. In particular, manufacturers of sonography equipment will need to provide control of basic console functions at each examination table, and to properly amplify signals from the scanhead so these can traverse an increased distance to the console. Installers will need to provide each scan site with a well-positioned viewing screen connected to the processing console. Electronic privacy will need to be assured by a switching mechanism whereby the processing console attends signals only from, and returns data only to, the site of the scan.

Expectant couples often seek to remember their prenatal experiences by documenting the ongoing life and progress of the developing fetus. For example, some patients bring a tape recorder and ask permission to record the Doppler sounds caused by fetal heart activity. Other patients request keepsake photographs or videotapes of some of the sonogram images of their fetuses. The current invention enhances patients' appreciation of a particular obstetric practice by fulfilling such desires. With minimal investment of time and attention from medical personnel, the patient herself may document the life and activity of her own fetus.

There are a number of other obstetrical, gynecologic, vascular surgical, or other medical instruments and supplies commonly used alongside Doppler or sonography equipment. These may include a container of ultrasonic conduction gel to enhance transmission of Doppler or sonogram signals across human body surfaces; a supply of tissue for wiping used ultrasonic gel from Doppler probe, ultrasound scanhead, or the patient; a discard basin for such tissue or other spent disposable items; a container of lubricating gel to enhance patient comfort during internal digital examinations; measuring tape in a retractable reel for determining uterine growth and size; a roll of pH-sensitive phenaphthazine ("nitrazine") test paper to determine whether rupture of the amniotic membranes has occurred; a due-date calculator wheel; a reflex hammer for evaluation of hypertensive conditions in and out of pregnancy; a penlight for close inspection of nail beds, pupils, or skin lesions; a writing instrument; a prescription pad; a pad of adhesive writing papers; and the patient's medical chart.

When these items are not in use, such as between two successive obstetric appointments in an office day, it is typical practice for various of these items (as in the case of the Doppler) to be stored in the pockets of the practitioner's lab coat, individually hand-carried, or left in or on cabinetry inside or outside the examination room. Moreover, nowadays many practitioners have dispensed with the wearing of laboratory coats with their storage pockets. Therefore obstetric instruments may have been strewn in locations inconvenient or unknown to the practitioner, who must either pause to personally retrieve these, or send his office assistant on a similar errand. Such unnecessary distractions waste office time, annoy assistants, and make the practitioner appear implement-oriented. They tend to deprive patient and caregiver of the satisfactions of a successful prenatal visit wherein the caregiver should have been enabled to focus fully on the patient and deal effectively with her concerns. Worse, the distracted or annoyed practitioner is prone to overlook some important detail of the patient's medical situation and commit a serious medical blunder.

A device or system for organizing obstetric implements is most useful if it helps the practitioner complete tasks smoothly, with little wasted motion. In each examination room the organizing system should arrange all implements in an unchanging compact array adjacent to practitioner and patient. In fact, attachment of the implement site to the examination table is desirable unless such interferes with operation of the examination table or hinders physical access to the patient.

Another concern of the caring practitioner is the temperature of lubricating and/or ultrasonic transmission gels that he applies from time to time to obstetric patients. Typically, ultrasonic conduction gel for abdominal Doppler or sonography is squeezed from a plastic container directly onto the bare abdomen of the patient. Direct skin application of this water-based gel, even at room temperature, causes a mildly jarring sensation akin to dripping cold water onto the body. Such discomfort is more notable during winter months when, due to the slight lowering of ambient office temperature, the temperature gradient between skin and gel increases, Similarly, non-heated lubricating gel applied directly to the patient's genitalia for a digital cervical exam adds the elements of surprise and discomfort to an experience which, for other reasons, the patient already expects to dislike. In any case, use of these substances at room temperature is inconsistent with the soothing environment which practitioners desire to create.

A known tactic is to warm such gel prior to direct skin application. A few practices employ freestanding countertop gel heaters in each examination room near an electrical outlet, not necessarily near the patient. Among currently available warmers, temperature set-point options are typically limited or absent, and no known model displays current gel temperature. The practical value of these existing models is therefore limited by paucity of gel temperature options, by cost (because convenience requires one in each exam room), and typically by remoteness of the gel heating site from the point of use. Some practitioners even resort to the quite unpredictable heating of gel bottles upon a conventional heating pad lining the bottom of a nearby cabinetry drawer.

There are prior art containers that are designed for heating medical products. U.S. Pat. No. 4,523,078 issued to Lehmann discloses a portable electrically heated container for transporting infusions. The container is shaped like a suitcase with a thermally insulated outer section and a heating element positioned inside the insulated portion. U.S. Pat. No. 5,183,994 issued to Bowles discloses a heated drug box that has a main compartment and a side compartment that is in thermal contact with a heater which can be connected to a power source and regulated by a temperature control. The side compartment is adapted for storage of intravenous solutions and is accessible without otherwise opening the drug box to the environment.

A significant number of obstetric patients develop blood pressure abnormalities which must be accurately monitored. Typically, the most reliable readings are obtained from patients lying supine or upon their left side. In the typical medical office, the obvious choice of furniture for such positioning is the examination table. The accuracy of blood pressure readings is further improved if the measuring device is positioned at the approximate height of the patient's body upon the examination table. An apparatus that allows positioning the blood pressure measuring device at approximately table top height adjacent the examination table would permit practitioners to more accurately monitor the patient's blood pressure.

Accordingly, what is needed and what is not found in the prior art is an apparatus for organizing, transporting, and facilitating the use of obstetrical and other medical devices and supplies with the following characteristics:

1. Portability of expensive, delicate, or misusable medical devices and supplies within one housing that may be reversibly and conveniently mounted at each examination site;
2. Compatibility with a wide range of commercially available hand-held Doppler devices, and/or integration of Doppler functions within the apparatus itself;
3. Compatibility with a wide range of commercially available sonogram scanheads and their associated electronic cabling and connectors;
4. Connectability to most conventional examination tables found in offices of obstetrics and gynecology;
5. Functionality from either side of the examination table, and for left- or right-handed practitioner;
6. Noninterference with operation of the examination table;
7. Noninterference with access to the examination of patients;
8. Convenient array of those medical devices and supplies necessary for the typical prenatal visit, without unreasonable duplication of expensive items;
9. Protection and security of medical implements especially vulnerable to unauthorized handling;
10. Accommodation of optional commonly used implements within the array;
11. Provision of adjustable warming of medical gels adjacent to the point of use;
12. Enablement of the patient to document for herself the life and activity of her fetus, with minimal expenditure of time and effort by medical personnel; and
13. Provision for blood pressure determinations when the patient can be positioned optimally for these readings.

An apparatus accomplishing such functions will offer medical personnel a welcome reduction in time, motion, petty frustration, and equipment repair or replacement. By helping medical personnel focus on patients, such apparatus should help to fulfill the fundamental desire of both patient and caregiver that care be provided with competence, efficiency, attentiveness, and warmth.

SUMMARY OF THE INVENTION

The present invention addresses the above-described problems by providing an apparatus for efficiently organizing, transporting, and using medical devices and supplies during obstetrical evaluations. Generally described, the present invention comprises a portable housing, a base housing, an alarm system, and a fixture mounting bracket. The portable housing preferably has a compartment for receiving and storing a medical device such as a Doppler device or a sonogram scanhead assembly and a compartment for receiving and storing medical supplies such as a gel bottle. The portable housing preferably has a mounting bracket and the base housing preferably has a mounting receptacle that removably couples with the portable housing mounting bracket for supporting the portable housing. The fixture mounting bracket removably attaches the base housing to an examination table or other fixture.

In a preferred embodiment of the present invention, the portable housing has a medical device compartment that may accept a Doppler receiving insert for use with a conventional Doppler device, that may accept an integral Doppler base unit customized for fitting in the compartment, or that may accept a scanhead receiving insert for use with a scanhead of a sonogram device. For use with a conventional Doppler device, a Doppler receiving insert is preferably arranged generally within the medical device compartment and generally adjacent to an alarm trigger device such as pressure sensitive contact switch for actuation thereof. The Doppler receiving insert may provide a shelf, a divider, and a bottom plate for forming a primary probe well for a primary probe of the Doppler device and a standby probe keep for a standby probe. The insert may have at least one security latch that engages at least one aperture in the bottom wall of the medical device compartment for removably securing the insert in place in multiple positions. An attachment mechanism may be provided such as a strap, magnetic strips, adhesive strips, or the like, for removably securing the Doppler base unit to the shelf.

The alarm system preferably additionally has a speaker, a volume control, and an on/off switch which may be positioned in another compartment for discreet activation of the alarm system, wherein the alarm system is electrically connectable to a power supply. A sensitivity adjustment mechanism is preferably provided for adjusting the sensitivity of the alarm to different types of Doppler devices having different sizes, shapes, and weights, the sensitivity adjustment mechanism preferably having an adjustment post on the Doppler receiving insert and a control rod capable of being generally telescopically rotated therein for extending and retracting the rod.

For use with an integral Doppler device, the medical device compartment may accept a customized integral Doppler base unit, with the base unit having at least one and preferably two wells for probes coupled to the base unit. The wells are preferably aligned with the trigger devices in the medical device compartment for alarm actuation. The integral Doppler base unit has an electric plug that electrically connects to a receptacle in the medical device compartment for power supply to the integral Doppler device.

For use with a sonogram device, a scanhead receiving insert is preferably arranged generally within the medical device compartment and generally adjacent to the alarm trigger device. The scanhead receiving insert preferably has an upper plate with a recessed portion for receiving and storing the scanhead and a notch for accepting the scanhead cable. The insert may have at least one and preferably two guide latches that engage the apertures in the bottom wall of the medical device compartment, and a spring or springs that bias the insert generally upward, for slidingly securing the insert in place in multiple positions.

The gel bottle compartment preferably has a gel heater arranged generally with a heater control electrically connected to the gel heater and the power supply, the heater control having at least one temperature sensor arranged generally proximate to the gel heater, at least one temperature readout, and at least one temperature set-point control. Power for the gel heater and/or the alarm system may be provided by connection to a conventional 120/240 VAC power source with an electric cord and plug or by a portable back-up battery in the portable housing. A control panel provides temperature readout, temperature set-point control, volume control, and power source selection.

Additional compartments, clips, or the like are preferably provided with the portable housing for storing medical items such as a tape measure, a roll of pH test tape, a prescription pad, a reflex hammer, due date calculator, medical chart, and/or a note pad. A carrying handle is preferably provided with the portable housing, the handle having an automatic lock/release mechanism for preventing movement of the handle from an upright position upon decoupling of the portable housing from the base housing.

The base housing preferably has two mounting receptacles, either of which removably couples with the mounting bracket of the portable housing. The base housing and portable housing each have electric contacts that are removably interconnectable for providing power and control wiring through the base housing to the gel heater and the alarm system. Also, for sonogram use, the base housing has a sonogram electrical connector that electrically connects to a sonogram electrical connector on the portable housing for providing power and control wiring from the sonogram console through the base housing to the sonogram scanhead, and for returning imaging signals from scanhead to console. Also, the base housing preferably has compartments for medical supplies generally needed in every examination room, such as for tissue and for waste. The fixture mounting bracket removably attaches the base housing to an examination table or other fixture.

There are preferably provided optional housings with each having a mounting bracket that removably couples with either mounting receptacle of the base housing, a mounting receptacle for receiving mounting brackets of other optional housings, and electric contacts for providing power and control wiring through the base housing to the particular optional housing. Preferably, a recording housing is provided with a audio/video player/recorder for recording Doppler-generated fetal audio and/or sonogram-generated fetal or maternal images. An auto-record system may be provided with an auto-record selector switch and signal contacts on the housings for connecting signal wiring through the base housing to the alarm trigger devices of the portable housing, so that the recording is automatically initiated upon removal of the Doppler probe or scanhead from its resting location on its insert. Also, a blood pressure housing is preferably provided with a compartment for storing a blood pressure cuff and with a control for operating the blood pressure cuff. Additionally, an endcap may be removably attached to the mounting receptacle of the last optional housing, for covering the contacts.

In use, the base housing is mounted to the examination table by the fixture mounting bracket and supplied with tissues and any other medical supplies commonly used in most examination rooms. Preferably, every examination room has a base housing installed to the table, with the base housing capable of being installed on either side of almost any known examination table. The portable housing may then be coupled to either side of the base housing as may be desired by the practitioner for use in the particular room, with the Doppler device or scanhead assembly mechanically secured in place and protected by an electric alarm. The practitioner may also conveniently access the temperature maintained gel bottle or other medical items as may be desired.

When the practitioner leaves the room, he may decouple the portable housing by lifting it generally upward. A carrying handle provides for ease of portability and has an automatic lock/release mechanism so that the handle locks generally upright when decoupled from the base and carried about. The back-up battery provides power to maintain the gel temperature while the portable housing is en route between rooms.

Accordingly, it is an object of the present invention to provide an apparatus for storing, organizing, transporting, and facilitating the use of medical implements and supplies commonly used during an obstetrical or other medical examination.

It is another object of the present invention to provide connectable interchangeable housings, each having dedicated compartments for storage of individual medical-related implements and supplies including audio and video recording devices, blood pressure determination devices, and the like, with detachable connectors providing portability for housings which accommodate expensive medical implements, thus obviating the need to furnish one of each implement in each and every examination room.

It is a further object of the present invention to provide an apparatus having a versatile mounting mechanism for attaching the apparatus to an examination table, and versatile connectors for attaching the housings together in various arrangements, such that the apparatus may be used with a wide variety of tables and commercial Doppler and sonogram equipment designs, from either side of the table, by either right- or left-handed practitioners, and with or without additional modular devices and stored implements.

It is still another object of the present invention to provide portable housings with protection and security mechanisms that protect implements such as a Doppler device and sonogram scanhead assembly from unauthorized handling and theft.

It is yet a further object of the present invention to provide a portable housing having a heating mechanism providing for continual warming and temperature maintenance of medical gels in accordance with an adjustable set-point, whether the housing is attached at tableside or in transit.

It is yet another object of the present invention to provide a portable housing for any commercially available hand-held Doppler device or sonogram scanhead assembly and a gel heater, and having universal housing brackets for removably attaching to universal housing receptacles of a base housing for tissue and waste, which is attached by an invertable fixture mounting bracket to an examination table, where the bracket and housing may be attached thereto, even for tables without underlying base cabinet.

Other objects, features, and advantages of the present invention will become apparent upon reading the following detailed description of embodiments of the invention, when taken in conjunction with the accompanying drawings and the appended claims.

BRIEF DESCRIPTION OF THE DRAWINGS

The invention is illustrated in the drawings in which like reference characters designate the same or similar parts throughout the figures, of which:

FIG. 8 is an elevation side view of a scanhead receiving insert and a conventional sonogram scanhead capable of use in conjunction with the portable housing;

FIG. 9 is an elevation endview of FIG. 8;

FIG. 16 is a detail side view of the carrying handle lock/release mechanism of the portable housing;

FIG. 17 is a detail cross section view taken at line 17—17 of FIG. 16;

DETAILED DESCRIPTION OF THE PREFERRED EMBODIMENTS

Figure 1:
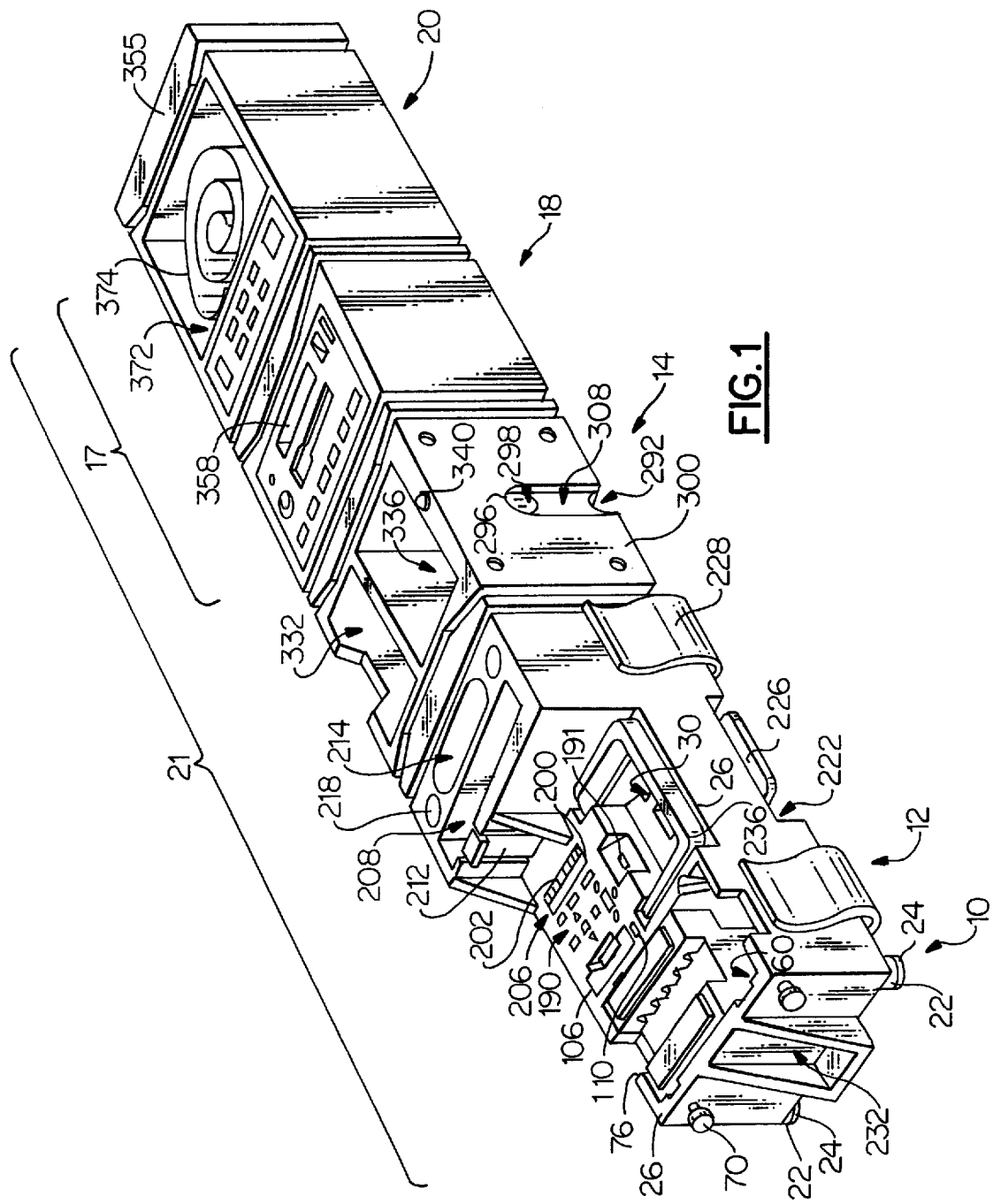
FIG. 1 is a perspective view of the present invention.
Figure 2:
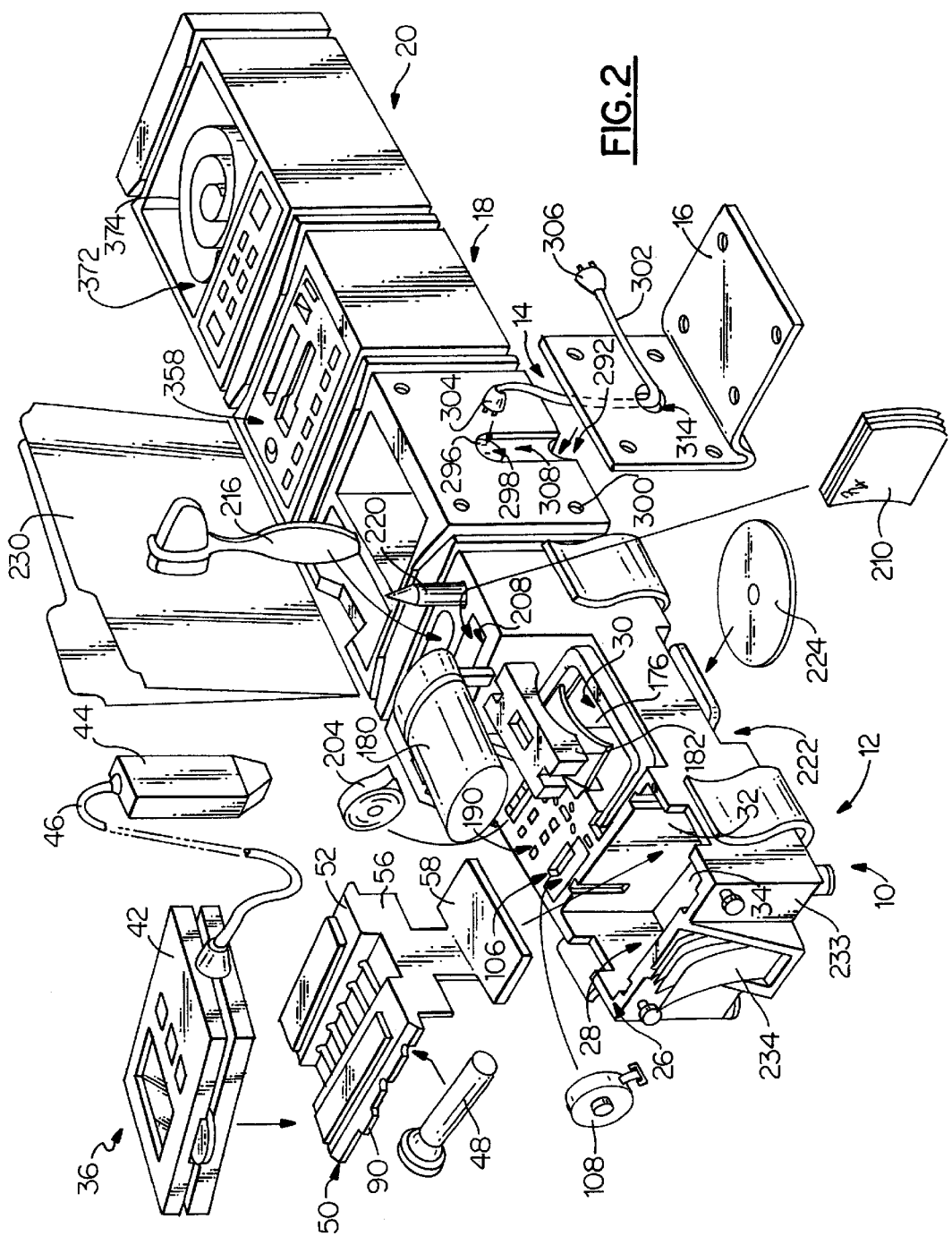
FIG. 2 is an exploded perspective view of the present invention and several medical implements and supplies typically used in conjunction therewith.

Referring to FIGS. 1 and 2, the present invention provides an apparatus 10 for organizing, transporting, and facilitating the use of medical devices and supplies. The apparatus 10 generally comprises a portable housing 12, a base housing 14, a fixture mounting bracket 16, and optional housings 17 such as an optional recording housing 18 and an optional blood pressure housing 20. As used hereinafter, the term "housings 21" collectively refers to the portable housing 12, the base housing 14, and the optional housings 17. It should be noted that the optional housings 17 may include the recording housing 18, the blood pressure housing 20, and other optional housings for medical implements and supplies contemplated by the present invention though not expressly described in detail herein.

The apparatus 10 is preferably provided with the portable housing 12 and base housing 14. Optionally, the portable housing 12 may be provided without the base housing 14 or any other type of structure for mounting thereto, the portable housing 12 may be provided without the base housing 14 and with a mounting bracket that removably receives the portable housing 12, the portable housing 12 may be provided with the base housing 14 and also with the optional housings 17, or the portable housing 12 may be provided in other configurations as desired for a given application.

The housings 21 are preferably constructed of a lightweight material such as plastic. Optionally, they may be constructed of metal, a composite, or other materials selected for high strength and low weight. The housings 21 are preferably generally rectangular or cuboidal in shape, though optionally they may be cylindrical, cylindroidal, ellipsoidal, or other regular or irregular shapes known to those skilled in the art.

The portable housing 12 preferably has at least one and most preferably four feet 22 extending generally downward therefrom for supporting the housing 12 on a generally horizontal surface (not shown). Each foot 22 may have a cap 24 or the like made of generally resilient material such as rubber or the like for providing a cushioning and/or no-slip effect.

The portable housing 12 preferably has an upper surface 26 with a plurality of compartments defined therein. Preferably, the portable housing 12 has a medical device compartment 28 and a gel bottle compartment 30. There may be provided optional compartments for storing other commonly used obstetrical, vascular, or other medical devices and supplies, as described hereinbelow.

Figure 3:
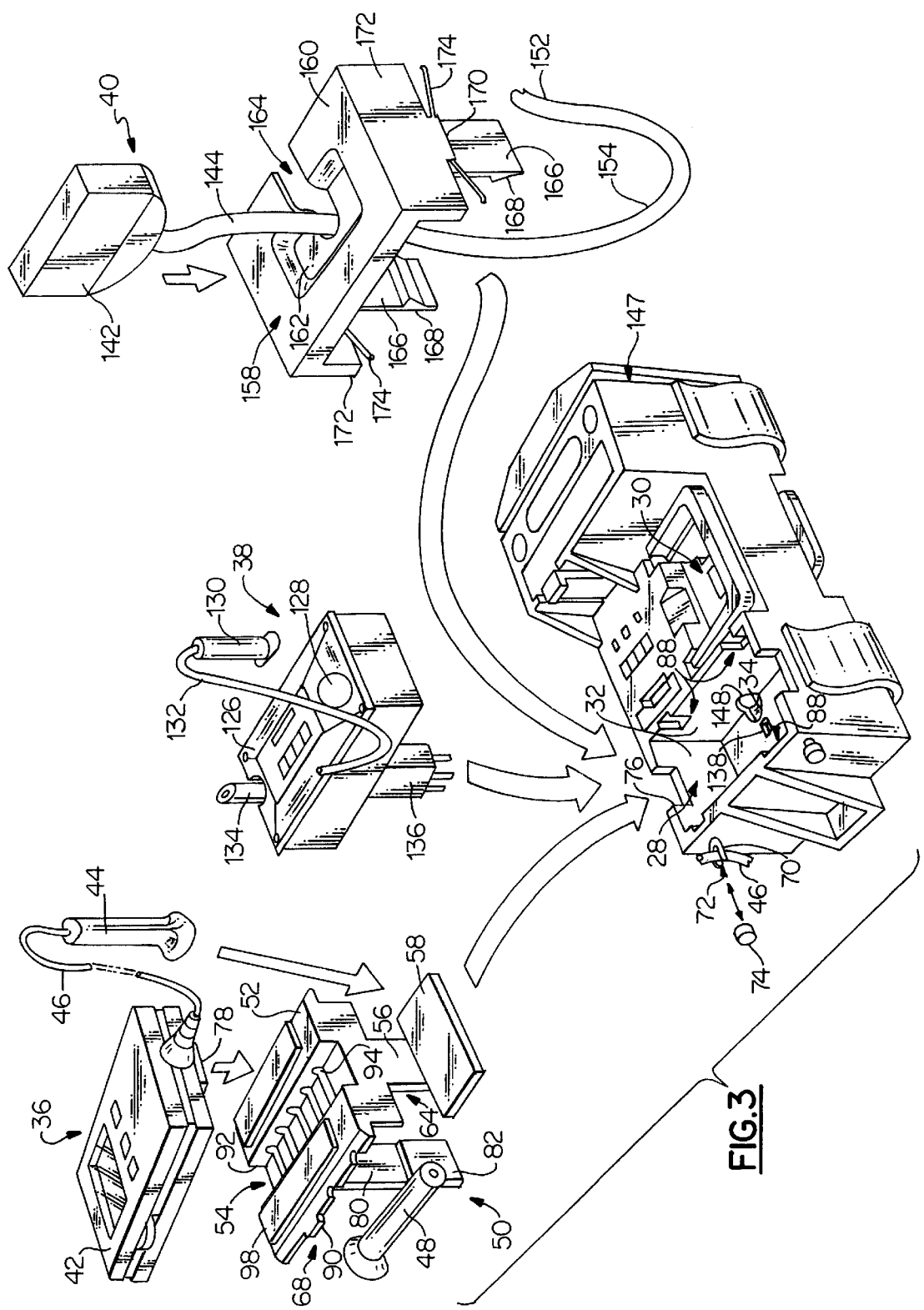
FIG. 3 is an exploded perspective view of a portable housing of the present invention and several medical implements capable of use in conjunction therewith.

Referring particularly to FIGS. 2 and 3, the medical device compartment 28 is preferably formed by four sidewalls 32 and a bottom wall 34. The medical device compartment 28 interchangeably accommodates any one of preferably at least three options in medical diagnostic equipment: conventional Doppler devices 36; integral Doppler devices 38; or conventional sonogram scanhead assemblies 40. Accommodation of the medical device compartment 28 to each of these three options is described, in turn.

The medical device compartment 28 accommodates a variety of conventional Doppler devices 36, including those having a Doppler base unit 42 connected to a primary probe 44 by a base-to-probe wire 46; Doppler devices 36 having these same three elements 42, 44, and 46 and also having separate standby probe 48, the wire 46 interchangeably disconnectable from the probes 44 and 48; and single-housing conventional Doppler devices (not shown) each having a base unit 42 which incorporates the functions of the primary probe 44 and as such requires no wire 46.

Figure 5:
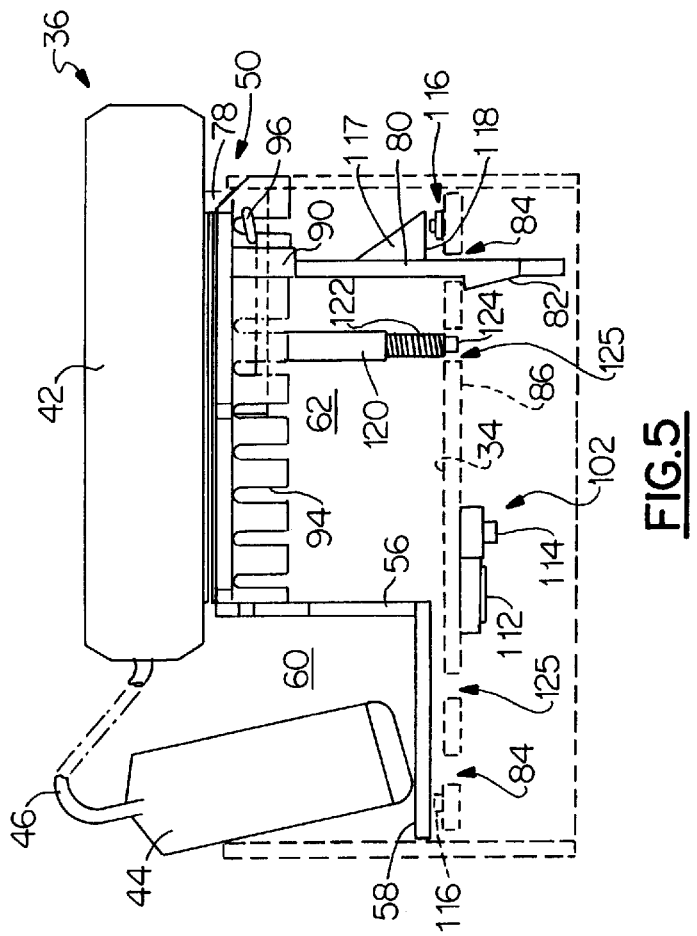
FIG. 5 is an elevation end view of FIG. 4 further showing a conventional Doppler device.
Figure 4:
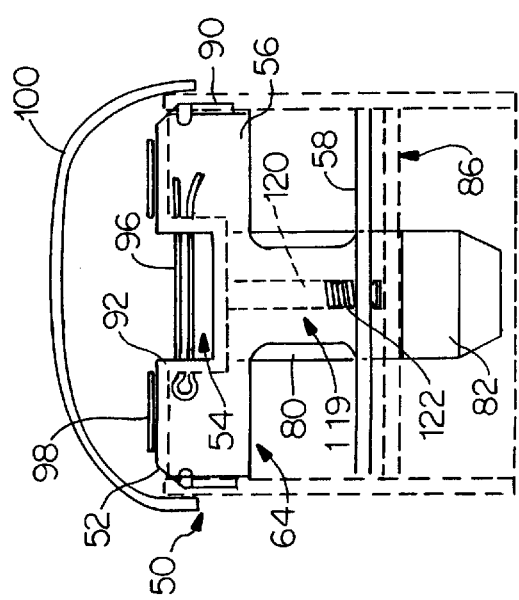
FIG. 4 is an elevation side view of a Doppler receiving insert capable of use in conjunction with the portable housing.

Referring to FIGS. 3–5, a removable Doppler receiving insert 50 is preferably arranged generally within the medical device compartment 28 for receiving and securing a conventional Doppler device 36 thereto. The insert 50 preferably comprises a mounting shelf 52 with a channel 54 defined therein, a divider panel 56 extending therefrom at an angle thereto, and a bottom plate 58 extending therefrom at an angle thereto, with the planes of the mounting shelf 52 and bottom plate 58 generally parallel and offset from each other and connected by the divider panel 56. Optionally, the Doppler receiving insert 50 may be provided in other configurations or the interior shape and contour of the medical device compartment 28 may be arranged to receive the Doppler device 36 so that the Doppler receiving insert 50 may be eliminated.

The mounting shelf 52 provides a location for storing and securing the Doppler base unit 42. The bottom plate 58 and divider panel 56 of the Doppler receiving insert 50, along with three sidewalls 32 of the medical device compartment 28, define a probe well 60 for storing primary probe 44. The mounting shelf 52, along with the bottom wall 34 and three sidewalls 32 of the medical device compartment 28, define a probe keep 62 for storing and protecting a standby probe 48. The divider panel 56 preferably has at least one panel opening 64 defined therein that allows extension therethrough of a lengthy standby probe 48 stored within the probe keep 62.

Figure 24:
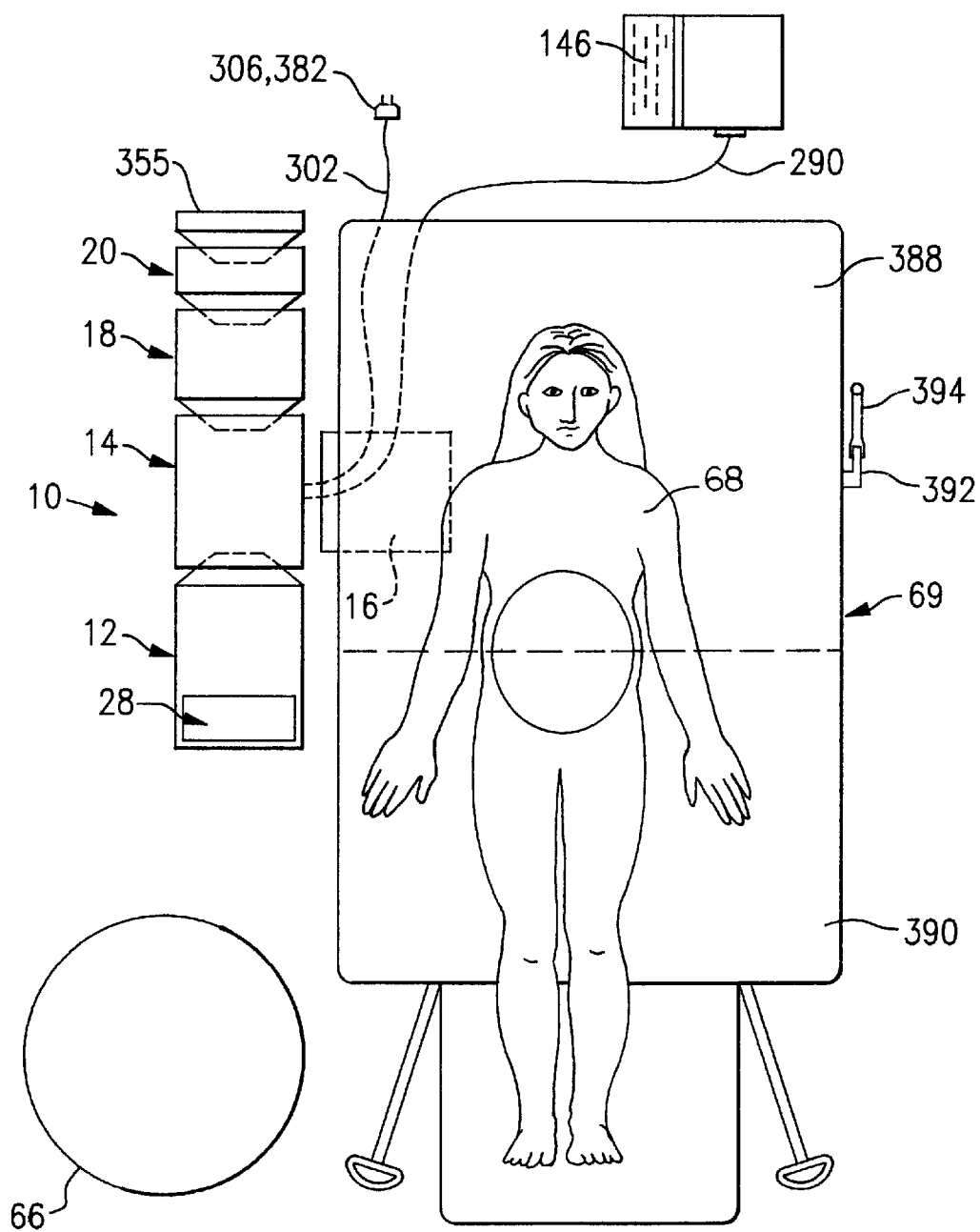
FIG. 24 is a top plan view of the present invention mounted to a conventional examination table.

The receiving insert 50 is located within the medical device compartment 28 so that the base unit 42 and the primary probe 44, are generally proximate to both a practitioner 66, and to a patient 68 on an examination table 69 (see FIG. 24). Also, preferably at least one Doppler wire attachment post 70 extends from the portable housing 12 generally proximate to the medical device compartment 28, with a notch 72 defined therein and a post cap 74 capable of being received thereon. The arrangement of the receiving insert 50 and the wire attachment post 70 thereby permit entrainment of Doppler base-to-probe wire 46 toward the exterior of portable housing 12. This entrainment prevents entanglement of the wire 46 with any devices or supplies housed elsewhere within the apparatus 10, particularly preventing wire 46 from complicating the placement of primary probe 44 into its probe well 60.

Medical device compartment 28 is preferably provided with at least one and most preferably two cutouts 76 defined therein, one in each of two opposing sidewalls 32 of the portable housing 12, each aligning with the channel 54 of the mounting shelf 52 of the Doppler receiving insert 50. Conventional Doppler devices 36 typically have a belt clip 78 formed thereon permitting removable attachment to a practitioner belt or the like. Cutouts 76 and channel 54 allow shelf 52 to accept Doppler base units 42 designed with belt clips 78 of any length.

At least one and preferably two security arms 80 each with a security latch 82 are preferably provided extending downward from the receiving insert 50, each latch 82 capable of being accepted by at least one and preferably two apertures 84 defined in the bottom wall 34 of the medical device compartment 28. The security arms 80 and security latches 82 preferably have the shape of a tongue, tab or slat, and the apertures 84 are preferably sized and shaped accordingly. Optionally, the security arms 80 and security latches 82 and the apertures 84 may be cylindrical, rectangular, or of another regular or irregular shape. The security arms 80 are preferably made of a material such as a plastic, metal, composite, or other material known to those skilled in the art and selected to provide elastic deformation sufficient to allow the arm latches 82 to be manually moved for engagement and disengagement with the bottom wall 34 generally adjacent the apertures 84.

When the security latches 82 are engaged with the bottom wall 34 generally adjacent the apertures 84, the latches 82 are concealed by the overlying insert 50 but nevertheless may be conveniently accessed from an undersurface 86 of the portable housing 12 by knowledgeable office staff, for release of Doppler device 36 and insert 50 from portable housing 12. Medical device compartment 28 is preferably provided with at least one and most preferably four recesses 88, two in each of two opposing sidewalls 32 and aligning with two tabs 90 extending from mounting shelf 52 of Doppler receiving insert 50. The security arms 80, security latches 82., and bottom wall apertures 84 are generally symmetrically arranged, and the tabs 90 and recesses 88 are generally symmetrically arranged, to permit the insert 50 to be removably secured within medical device compartment 28 in either of two positions, the first position being at 180 degrees relative to the second position. Optionally, the receiving insert 50 can be fixed in place by screws, bolts, pins, clamps, an adhesive, or the like.

Protection of Doppler device 36 by the apparatus 10 is preferably provided by mechanical attachment and/or electrical alarm mechanisms. The mounting shelf 52 of receiving insert 50 provides for several methods of fastening Doppler base unit 42 thereto. Preferably, the channel 54 of the shelf 52 is formed by sidewalls 92 each having at least one channel aperture 94 defined therein and aligned for receiving therethrough a belt clip pin 96 for capturing the Doppler belt clip 78 of Doppler base unit 42. For accommodating a Doppler device 36 without a belt clip 78, there may optionally be provided a block, disc, or the like (not shown) with an adhesive backing or other attachment to the Doppler device 36 and with an aperture defined therein for receiving the belt clip pin 96. Optionally, the Doppler base unit 42 may be secured to receiving insert 50 by a strap (not shown) for securing Doppler belt clip 78 to a portion of receiving channel 54, by at least one magnetic, hook-and-loop, or adhesive strip 98 attached to base unit 42 and to a top surface of the mounting shelf 52, or by an elastic strap 100 for disposing around the entire base unit 42 and removably connecting to the insert 50, by any combination of these, or by other fastening methods known to those skilled in the art. Base unit 42 of the Doppler device 36 is thus physically secured to the insert 50, yet knowledgeable practitioners contemplating repair or battery replacement of Doppler equipment can readily remove Doppler receiving insert 50 from medical device compartment 28 and thereby access the attachment points of these various Doppler binding devices beneath receiving insert 50.

An alarm system 102 preferably comprises at least one alarm on/off switch 104 (see FIG. 23) or the like permitting disablement of the alarm system 102 when, for example, the practitioner 66 prepares to manipulate Doppler device 36, 38 or another alarm-protected item. The alarm system 102 is electrically connected to at least one power supply such as an external power supply 140 and/or an internal portable power supply 198 (see FIG. 23) as described hereinbelow. The alarm on/off switch 104 is preferably positioned within a measuring tape compartment 106 which houses a measuring tape 108 (as described hereinbelow). The switch 104 is concealed by the measuring tape 108 which allows the practitioner 66 to enable or disable the alarm system by an inapparent technique. The practitioner 66 actuates the switch 104 to enable the alarm system 102 by moving the measuring tape 108 within the compartment 106 to contact and depress or to release the alarm on/off switch 104.

An alarm system indicator light 110 is electrically connected to the on/off switch 104 and provides a visual indication of whether the system 102 is enabled. Additional components of alarm system 102 are preferably provided on portable housing undersurface 86 and include a speaker 112, bell, buzzer or other sound emitting device, a volume control 114 having a dial, pushbutton, slide knob, or the like, and conventional electric circuitry for the electrical operation thereof.

The alarm system 102 has at least one triggering device 116 preferably located generally within medical device compartment 28. Such triggering device 116 preferably comprises at least one and preferably two conventional pressure sensitive contact switches 116 arranged on bottom wall 34 of medical device compartment 28 at a location generally subjacent to bottom plate 58. Two contact switches 116 are arranged generally at opposite ends of the compartment 28 so that the insert 50 therein may be oriented in either of two positions at 180 degrees from each other. Tampering with or removal of Doppler primary probe 44 and/or base unit 42 from the portable housing 12 relieves pressure of bottom plate 58 from switch 116, allowing biased opening or closing of the contacts of switch 116 to actuate the system 102 to sound the speaker 112.

Where more than one contact switch 116 is provided, release of any one contact switch or switches 116 sounds the alarm speaker. To prevent the alarm from sounding continuously, a tab 117 or post is provided on insert 50, with a contact surface 118, which continually depresses any additional contact switches in compartment 28 while insert 50 is installed therein. The enabled alarm system 102 thereby sounds an alarm from speaker 112 when any component of the associated Doppler device 36 is removed or tampered with.

Triggering of the alarm depends upon changes in weight or weight distribution of components of the particular Doppler device 36 deployed upon receiving insert 50. To account for design differences among Doppler devices 36, the alarm system 102 preferably has a sensitivity adjustment mechanism 119.

The sensitivity adjustment mechanism 119 preferred comprises a generally hollow, internally threaded adjustment post 120 extending generally downward from mounting shelf 52 of insert 50. A sensitivity control rod 122 is preferably provided with external threads capable of mating with the internal threads of the post 120 so that at least a portion of the rod 122 may be telescopically and rotationally extended from and retracted into the post 120. The rod 122 preferably has a head 124 which is supported on the bottom wall 34 and/or extends at least partially through at least one sensitivity control aperture 125 defined therein. Two or more of the apertures 126 are preferably provided and arranged generally symmetrically and at opposite ends of the Doppler/scanhead compartment 28 so that the insert 50 may be oriented within it in either of two positions at 180 degrees from each other. The rod 122 is preferably provided as a conventional screw, and the head 124 and aperture 125 preferably have mating beveled sides with roughened surfaces to frictionally prevent rod 122 from rotating freely within post 120 and allowing the sensitivity adjustment mechanism 119 thus to drift out of adjustment.

Rotation of sensitivity control rod 122, for example by a wrench, screwdriver or the like, causes the rod 122 to extend further from or retract further into the post 120, thereby increasing or decreasing the length of the portion of rod 122 extending from the post 120. The switch 116 beneath bottom plate 58, and the post/rod assembly 120/122, are each generally off-center and opposite each other within the compartment 28, and the insert 50 is made of a sufficiently pliable material so that the weight of the Doppler device 36 on the mounting shelf 52 and/or the weight of the primary probe 44 on the bottom plate 58 may cause the bottom plate to flex slightly downward beyond the support of the fixed post 120 and rod 122. This arrangement allows the practitioner 66, by rotating sensitivity control rod 122, to adjust the position of the bottom plate 58 of insert 50 relative to the bottom wall 34 of medical device compartment 28 as desired to counterbalance the weight of any conventional Doppler device 36 (with or without separate probe 44) borne upon insert 50. With the above described sensitivity adjustment mechanism 119 properly adjusted, the weight of the Doppler device 36 upon the insert 50 generally deflects at least a portion of the insert 50 downward to depress contact switch 116, and removal or any slight upward movement of any portion of the Doppler device 36 allows the contact switch 116 to be released.

The sensitivity of the contact switch 115 of the triggering mechanism of alarm system 102 is conveniently adjusted as follows. First, all components of the conventional Doppler device 36 (primary probe 44, base unit 42, and base-to-probe wire 46) are installed upon Doppler receiving insert 50, which is then latched within medical device compartment 28. Next, sensitivity control rod 122 is rotated until bottom plate 58 of insert 50 applies upon the underlying contact switch 116 a minimum pressure necessary to silence speaker 112.

Optionally, the alarm may be provided by an alarm system 102 having other trigger devices 116 such as a contact attached directly to the Doppler device 36 and an oppositely aligned contact attached directly to the receiving insert 50 and where movement of the Doppler device 36 relative to the receiving insert 50 similarly opens or closes the circuit and triggers the speaker 112; by a transmitter in the base unit 42 and a receiver in the probe 44 with a speaker 112 triggered by a predetermined distance separation between the two; by a circuit having a photoelectric sensor situated within medical device compartment 28, such that removal of either the in-use probe 44 or the base unit 42 from its respective resting location increases the flux of photons at the sensor triggering the speaker 112; by biometric identification or other practitioner 66 recognition systems identifying the practitioner's voice, retina, fingerprint, and the like, that trigger speaker 112 when the Doppler device 36 is handled by an unauthorized person; by the preferred alarm system 102 described hereinabove except with alternate adjustment means comprising electric circuitry and pushbutton or like controls; or by other alarm systems and trigger devices known to those skilled in the art.

The speaker 112 or like device on the portable housing undersurface 86 converts the electric alarm signal into sound waves, and also may convert the fetal signal from the integral Doppler device 38 (described hereafter) into sound waves. The volume control 114 permits adjustment of the speaker 112 volume to provide a sound sufficiently loud to alert the practitioner 66 yet not frighten anyone. Optionally, the alarm system may be provided with a vibration alarm by including a transmitter for sending a signal to a vibrating pager worn by the practitioner 66, by energizing a flashing light, or by other visual, sound, touch, or other alarm methods known to those skilled in the art.

The combination of mechanical attachments and alarm system 102 allows generally all conventional Doppler devices 36 stability during repositioning of portable housing 12, easy removal of probe components for application to patients, and protection from tampering or theft. The alarm system 102 is especially beneficial for protection of Doppler devices 36 having probe 44 and base unit 42 combined as a single housing, and for protection of Doppler devices 36 which employ a remote base unit 42 and therefore allow only probe 44 to be located in medical device compartment 28. These two particular subgroups of commercial Doppler device 36 generally cannot be conveniently protected by mechanical attachment methods since, in each case, use of such devices in patient care regularly necessitates detachment of all accommodated elements of Doppler device 36 from medical device compartment 28. The manner in which alarm system 102 may be adapted to protect integral Doppler 38 is explained hereinbelow.

Figure 7:
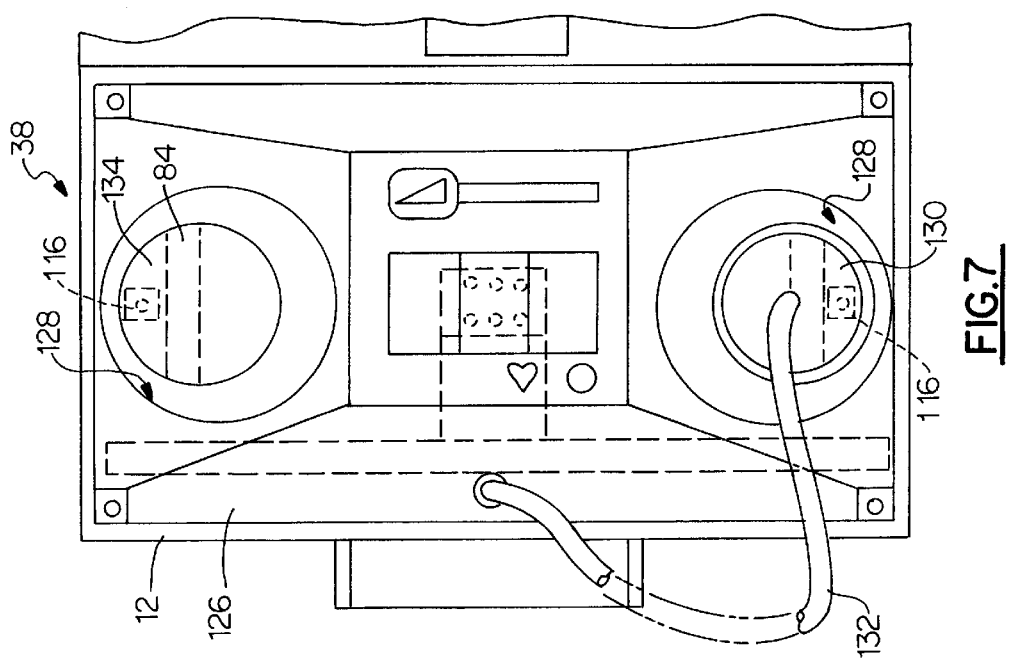
FIG. 7 is a top plan view of FIG. 6.
Figure 6:
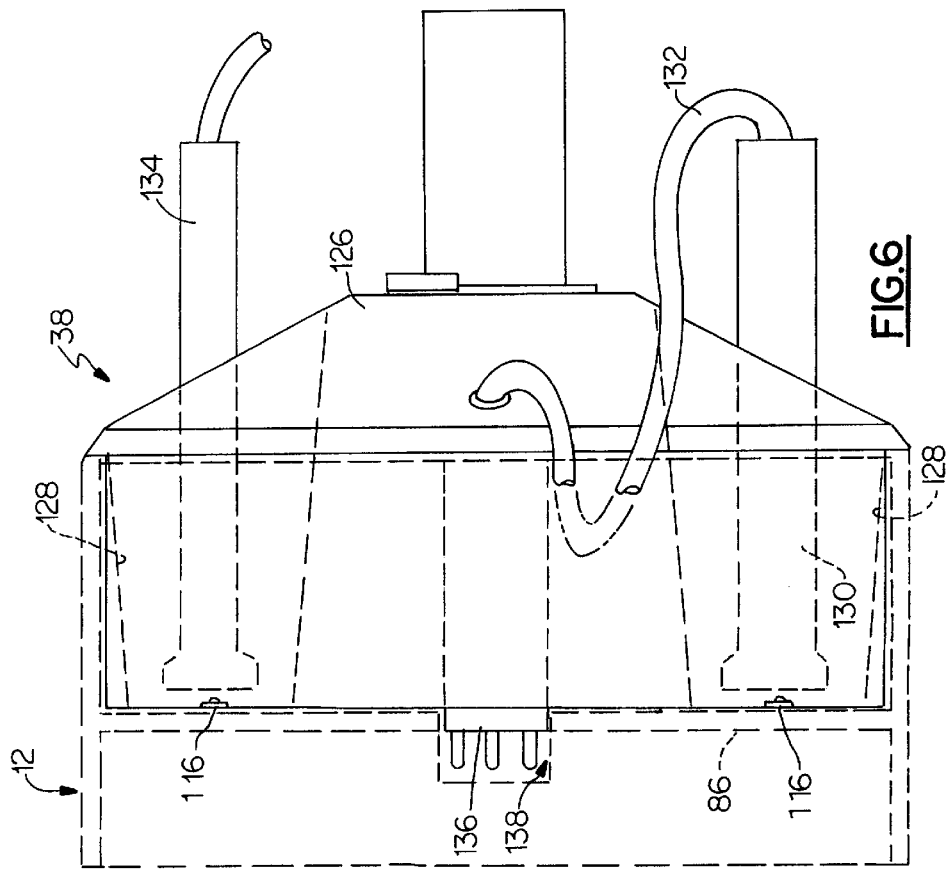
FIG. 6 is an elevation side view of an integral Doppler capable of use in conjunction with the portable housing.
Figure 10:
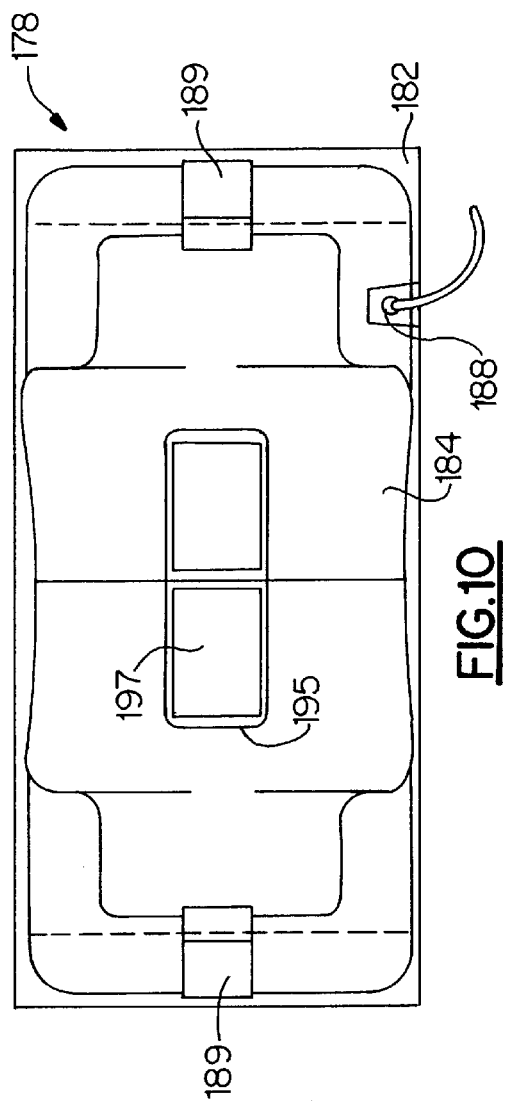
FIG. 10 is a top plan view of the gel heater block of the portable housing.
Figure 12:
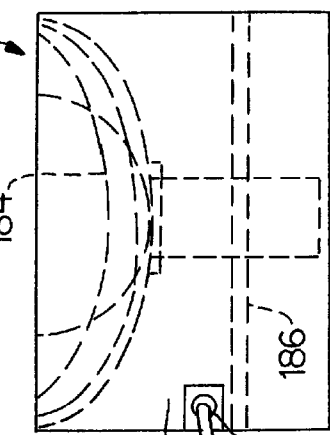
FIG. 12 is an elevation end view of FIG. 10.
Figure 11:
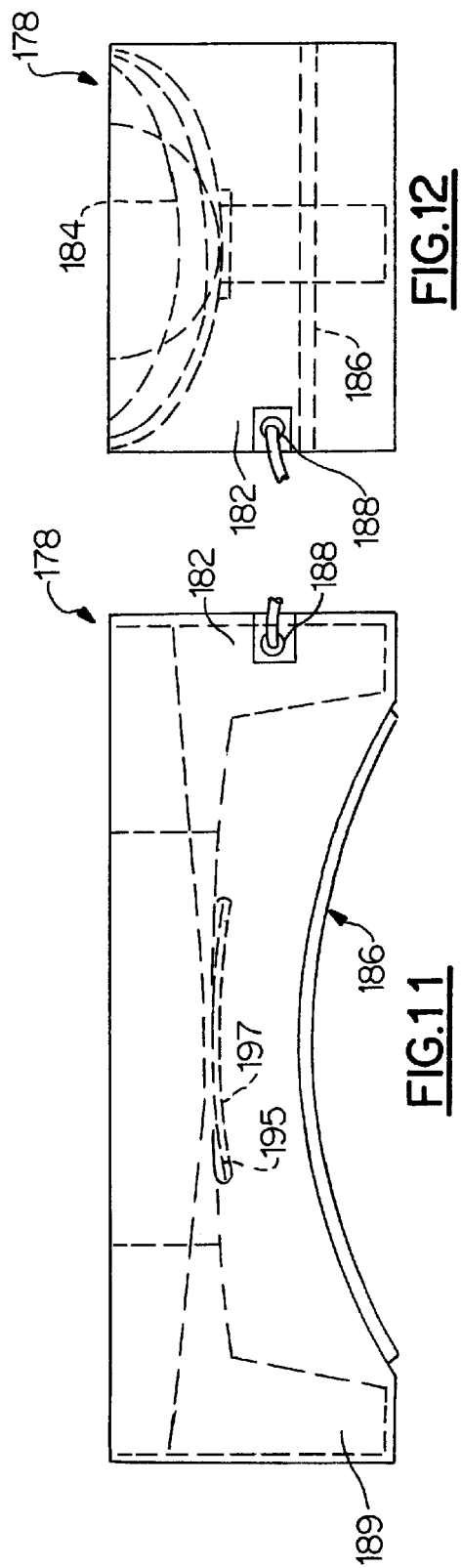
FIG. 11 is an elevation side view of FIG. 10.

Referring to FIGS. 3 and 6–7, medical device compartment 28 can alternatively receive and store the integral Doppler device 38 which has a base unit 126 integrally formed with or mounted into the compartment 28. The integral base unit 126 is sized and shaped to be removably received generally within the compartment 28, and may be secured in place by screws, nuts and bolts, bracketry, and/or other fasteners known to those skilled in the art. The base unit 126 is preferably provided of a plastic, metal, composite, or other material known to those skilled in the art.

The base unit 126 has at least one and preferably two integral probe wells 128 defined therein for accepting a primary probe 130 with a base-to-probe wire 132 and a standby probe 134, the wire 132 interchangeably disconnectable from the probes 130 and 134. The probe wells 128 are preferably generally aligned with contact switches 116 of portable housing 12 so that insertion therein of primary and/or standby probe 130, 134 depresses the corresponding contact switch 116 to silence the alarm speaker 112 and removal of primary and/or standby probe 130, 134 from the corresponding well 128 releases the corresponding contact switch 116 to sound the speaker 112. Optionally, an automatic on/off Doppler circuit 135 may be wired to the contact switches 116 so that, regardless of whether the alarm system 102 is recruited by its alarm on/off switch 104, removal of either one of the probes 130, 134 closes the power circuit to electrically energize the Doppler device 38 for detection of fetal life, and insertion of the probe 130, 134 opens and de-energizes the circuit. An integral Doppler electrical plug 136 is provided preferably extending from base unit 126 and an integral Doppler electrical receptacle 138 is provided preferably defined in medical device compartment 28 for receiving the plug 136, with the receptacle 138 electrically connected to the external power supply 140 and/or the internal portable power supply 198 (see FIG. 23) as described hereinbelow.

Integration of Doppler base unit 126 into the portable housing 12 confers several advantages relative to use of conventional Doppler devices 36. Firstly, this integration protects the Doppler equipment more effectively than in the case of a conventional Doppler device 36, because integral Doppler base unit 126, essential to the function of the associated probes 130, 134 and wire 132, is not removable from the portable housing 12 without appropriate tools. Secondly, the integral Doppler electrical plug 136 and receptacle 138 allow integral Doppler device 38 to operate on the external power supply 140 or portable back-up battery 198 of the apparatus 10, thereby eliminating the need for an independent power source (such as batteries) within integral Doppler 38. Thirdly, alignment of probe wells 128 over contact switches 116 of portable housing 12 allows removal and insertion of either probe 130, 134 from the corresponding well 128 to sound and silence the speaker 112 of the alarm system 102 and/or to automatically energize and de-energize the Doppler device 38. Fourthly, integral Doppler device 38 is sized and shaped to fit within the selfsame compartment 28 which receives the insert 50 for the conventional Doppler device 36, so that if the conventional 36 or integral 38 Doppler device needs replacement, the practitioner 66 may retrofit the apparatus 10 with his preference of conventional 36 or integral 38 Doppler device, without needing to replace the entire apparatus 10.

Referring to FIGS. 3 and 8–9, medical device compartment 28 can alternatively receive and store the conventional sonogram scanhead assembly 40 for use of the present invention 10 in transabdominal and/or transvaginal sonography. The sonogram scanhead assembly 40 generally comprises a scanhead 142 having a cable 144 connected thereto with an electrical plug 145 (see FIG. 18), jack, computer-style, coupling, or connector connected to the opposite end of the cable 144 for communication with a sonogram console 146 (see FIG. 24). A dedicated route for the scan cable 142 is preferably provided from the compartment 28 through and/or upon exterior surfaces of portable housing 12 and to a bracket endwall 147 of the portable housing 12. Preferably, a cable aperture 148 is defined in one sidewall 32 of compartment 28 and a cable channel 150 is defined in the portable housing undersurface 86 and in communication with the cable aperture 148, for entraining a first portion 152 of scan cable 144 therethrough. A second portion 154 of scan cable 144 may have a segment that hangs in a scan cable loop beneath medical device compartment 28, available to be extended therefrom or retracted therein as desired in the use of the scanhead 142. The total length of scan cable 144 is preferably selected to provide the second portion 154 sufficiently long to permit proper access of sonogram scanhead 142 to patient 68 positioned upon the adjacent examination table 69 and the second portion 154 sufficiently short that when sonogram scanhead 142 is returned to medical device compartment 28, the practitioner 66 will not tread upon it or become entangled by it.

There is preferably provided for use with the sonogram scanhead assembly 40 a scanhead receiving insert 158 which may be received by the medical device compartment 28. Scanhead receiving insert 158 provides a protective niche for the fragile and expensive sonogram scanhead 142, allows convenient management of scan cable cable 144, and participates in triggering alarm system 102 when the sonogram scanhead 142 is removed from the scanhead receiving insert 158 by an unauthorized person. Optionally, the scanhead receiving insert 158 may be provided in other configurations or the interior shape and contour of the medical device compartment 28 may be arranged to receive the scanhead assembly 40 so that the scanhead receiving insert 158 may be eliminated.

Scanhead receiving insert 158 preferably has an upper plate 160 sized and shaped to be removably received generally within the compartment 28. Upper plate 160 preferably has a recess 162 defined generally centrally therein for receiving the sonogram scanhead 142. A cable notch 164 is defined in upper plate 160, preferably extending into at least a portion of the recess 162. The cable notch 164 is preferably sized to receive the second portion 154 of the scan cable 144 and allow it to be extended or retracted therethrough in accordance with scanhead 142 withdrawal from or replacement into recess 162. The cable notch 164 also permits the scan cable 144 to be received laterally therein and removed laterally therefrom when the insert 158 is first removed from the compartment 28, for purposes of repair or replacement of the entire sonogram scanhead assembly 40. The bottom wall 34 of the portable housing 12 preferably has an opening 165 defined therein for receiving therethrough the scan cable 144; and this opening 165 and the contiguous cable aperture 148 are together large enough to extend therethrough the scanhead electrical plug 145 for installation and removal of scanhead assembly 40.

At least one and preferably two guide arms 166 are provided extending from the plate 160 with each having at least one guide latch 168. The two guide arms 166 and latches 168 are arranged so as to be capable of generally aligning with and extending through bottom wall apertures 84 so that the latches 168 engage portable housing undersurface 86 adjacent the apertures 84 to limit upward movement of the insert 158 so that it is retained generally within medical device compartment 28. The guide arms 166 are preferably made of a material such as a plastic, metal, composite, or other material known to those skilled in the art and selected to provide elastic deformation sufficient to allow the guide latches 168 to be manually moved for engagement and disengagement with the bottom wall 34 generally adjacent the apertures 84. The engaged guide latches 168 are concealed by upper plate 160 of scanhead receiving insert 158, but latches 168 and apertures 84 may be conveniently disengaged by accessing guide latches 168 at the portable housing undersurface 86.

Scanhead receiving insert 158 may function with alarm system 102 to provide security for scanhead assembly 40. At least one and preferably two contact surfaces 170 are formed on the upper plate 160, or on panels 172 extending from the upper plate 160, and capable of aligning and engaging the contact switches 116 of the portable housing 12. At least one and preferably four springs 174 are provided extending from the upper plate 160 or panels 172 to bias the insert 158 generally upward. The springs 174 are preferably provided by extension arms made of a metal, plastic, composite, or other resilient material known to those skilled in the art. Optionally, helical springs, resilient solid members, or other spring mechanisms known to those skilled in the art may be suitably employed.

The springs 174 are selected with an elasticity such that they contact bottom wall 34 of medical device compartment 28 and maintain the empty scanhead receiving insert 158 in a position at the upper limit of vertical travel allowed by guide latches 168, and such that the weight of sonogram scanhead 142 upon the insert 158 causes the springs 174 to compress and the scanhead receiving insert 158 to descend a slight distance within medical device compartment 28 sufficient for the contact surface 170 to operate the contact switches 116 of the portable housing 12. Thus, the weight of the sonogram scanhead 142 upon the insert 158 generally compresses the springs 172 downward so that the contact surfaces 170 depress and operate the contact switches 116 to silence the alarm speaker 112, and removal or any slight upward movement of any portion of the scanhead 142 allows the contact switches 116 to be released, which sounds the alarm speaker 112.

The scanhead receiving insert 158 may be provided of a generally rigid material such as a plastic, metal, composite, or other material known to those skilled in the art. It should be noted that insert 158 is allowed to move within the medical device compartment 28 generally vertically a relatively small distance as necessary to engage the contact switches 116 and operate the alarm system 102, in contrast to the Doppler receiving insert 50 which has the adjustment post 120 and control rod 122 which generally eliminate any vertical movement of the Doppler receiving insert 50 within the medical device compartment 28 as the insert 50 is provided with a flexibility sufficient to deflect as necessary to engage and operate the contact switches 116. It should be further noted that, in contrast to the variety of potential weight distributions of conventional Doppler base units 42 and primary probes 44 upon Doppler receiving insert 50, weight loading of scanhead receiving insert 158 is all-or-none. Consequently, with proper choice of elasticity of springs 174, scanhead receiving insert 158 will descend under the weight of any sonogram scanhead 142. Scanhead receiving insert 158 therefore requires no alarm sensitivity adjustment mechanism 119.

Turning now to the gel bottle compartment 30, and referring to FIGS. 1, 2, and 10–12, there are preferably provided gel bottle compartment sidewalls 176 that define the gel bottle compartment 30. The compartment 30 preferably contains a gel heater 178 for warming a removable gel container 180 of ultrasonic conduction and/or lubricating gel. Preferably, the gel heater 178 comprises a block 182 made of aluminum or a like thermal conductive material (see FIGS. 10–12). The block 182 preferably has a concave upper surface 184 and the gel container 180 preferably has a surface 181 with a curvature generally conforming to the concave surface 184 of the block 182 to provide for a maximum contact area of surfaces 181 and 184 for heat transfer to gel container 180.

An electric resistance heating element 186 or the like is arranged generally underneath the aluminum block 182 for generating heat therefor. Optionally, heating may be provided by a metallic or ceramic plate, by a like heating element for low-output electrical resistance heating, by microwave application, by air or water convection, or by other heating methods known to those skilled in the art.

A heater circuit 187 (see FIG. 23) comprises electric resistance heating element 186 and a temperature sensor 188 positioned generally within or adjacent to aluminum block 182. A control panel 190, preferably arranged upon the upper surface 26 of portable housing 12 adjacent gel bottle compartment 30 preferably comprises a heater indicator light 191, a temperature readout 192 for the current temperature of aluminum block 182 according to the temperature sensor 188 and/or for the gel temperature set-point selected using a temperature set-point control 193 operated by at least one knob, button, dial, slide lever, or the like. The control panel 190 preferably provides a digital and/or analog readout 192 in Centigrade and/or Fahrenheit units.

By adjustment of the temperature set-point control knob, the practitioner 66 may select a desirable temperature based upon maternity clothing styles typical of the season, the ambient office temperature, and any stated preferences of prior patients 68. The heater control 187 operates to energize heating element 186 whenever the temperature of aluminum block 182 falls below the set-point temperature selected by the practitioner 66. Optionally, the gel heater 178 may be provided with a heater control 187 providing timed cycle operation, overheat protection, various display options, and the like.

The control panel 190 preferably also has a power source selector 194 (see FIG. 23) having a dial or the like electrically connected to the external power supply 140 and the portable power supply 198 for choosing an electric power source for the gel heater 178 and/or the integral Doppler device 38. The external power supply 140 may be provided by conventional 120/240 VAC, low-voltage direct current, batteries, or other power sources known to those skilled in the art. The portable back-up power supply 198 (see FIG. 23) may be provided by a rechargeable or replaceable battery preferably provided within the portable housing 12 to supplement line-source gel heating whenever the portable housing 12 is detached from the base housing 14. The selector dial permits at least these gel heating power source options: withholding all power from the gel heater (no power), providing power from the line source only (external/line power), or utilizing the back-up power supply 198 by default if line power is unavailable.

Figure 13:
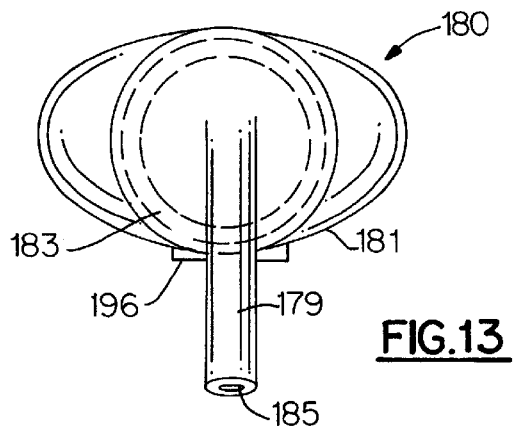
FIG. 13 is an elevation end view of the gel container of the portable housing.
Figure 14:
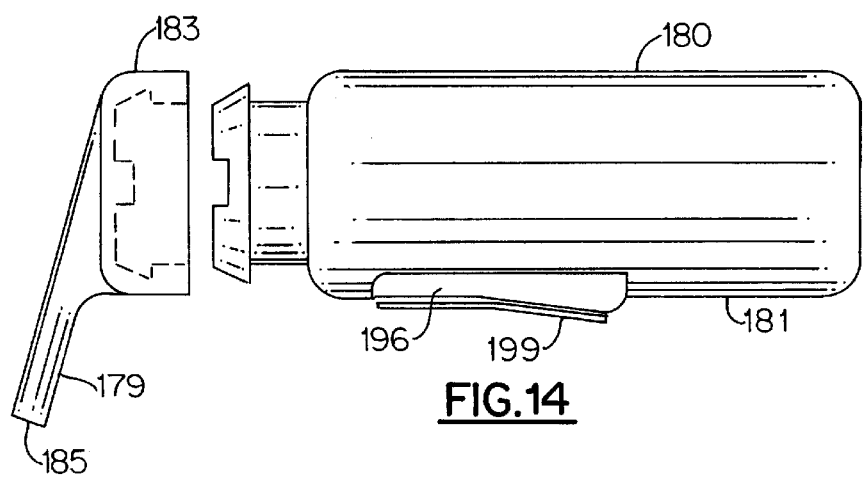
FIG. 14 is an elevation side view of FIG. 13.
Figure 15:
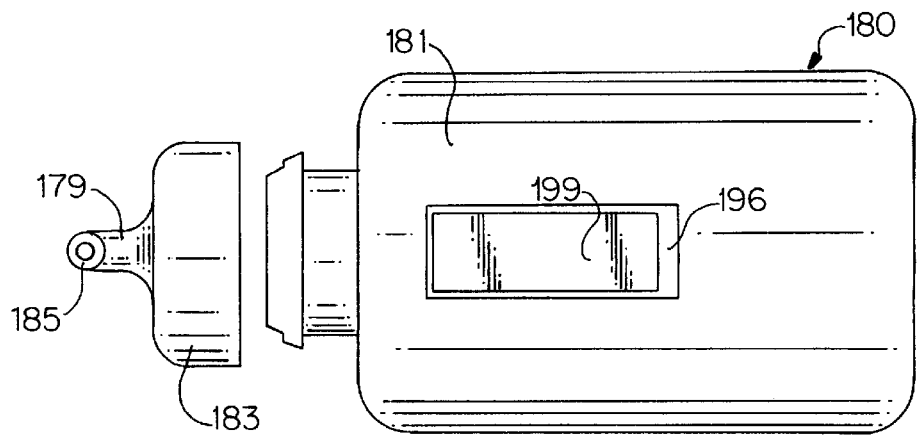
FIG. 15 is a bottom plan view of FIG. 13.

Referring now to FIGS. 13–15, the disposable gel container 180 is preferably made of a material and in a shape providing heat transfer characteristics for quickly achieving and accurately maintaining gel temperature. The curvature of the surface 181 of the disposable gel container 180 is preferably selected to generally conform to the gel heater 178 as described hereinabove and further to be comfortable to the practitioner's 66 hand. The gel container 180 is preferably provided with a detachable cap 183 so that the container 180 may be refilled with gel as may be desired. The cap 183 preferably has an extension arm 179 with a dispensing port 185 defined therein and arranged to be generally at the lowest point of the gel container 180 as it is stored generally horizontally on the aluminum block 182. The shape, port location, and storage position of gel container 180 act to gravitationally urge contained gel toward dispensing port 185 to maximize the gel volume dispensable from a nearly spent gel container 180. The block 182 preferably has at least one extension arm cavity 189 defined therein for receiving the extension arm 179 of cap 183 and at least one recess 195 defined therein for receiving a projection 196 extending from bottle 180. Adhesive strips 197 and 199 such as magnets, hook and loop fasteners, or other fastening devices known to those skilled in the art are arranged within the recess 195 and attached to the projection 196 to assist in maintaining gel bottle 180 upon block 182 when portable housing 12 is carried or repositioned.

Referring back to FIGS. 1 and 2, the portable housing 12 preferably has additional compartments defined therein for additional devices and supplies routinely used in a prenatal visit. The measuring tape compartment 106 (mentioned hereinabove for housing and concealing alarm on/off switch 104) is preferably provided for receiving a conventional reel of measuring tape 108. A pH test tape compartment 200 with a removable compartment cover 202 is preferably provided for receiving a conventional phenaphthazine paper roll 204 for acidity testing of vaginal fluids. The compartment cover 202 is preferably generally opaque for protecting the paper roll 204 from the damaging effects of light, has a color-to-pH legend thereon for interpretation of acidity test results, and has a saw-toothed edge 216 for detaching tape from the phenaphthazine paper roll 204.

A prescription pad compartment 208 is preferably provided for receiving a conventional prescription pad 210. Preferably, the prescription pad compartment 208 has a depth sufficient to receive and render inaccessible the prescription pad 210. A generally vertical slide member 212 is provided on the portable housing 12 and has a tab or the like (not shown) extending into the pad compartment 208, so that the slide member 212 is capable of engaging and elevating the prescription pad 210. Prescription pad compartment 208 and slide member 212 maintain prescription pad 210 out of sight and reach, but enable the practitioner 66 to retrieve it easily. An alarm on/off switch 213 (see FIG. 23) similar to contact switch 116 is preferably provided in a bottom wall of the prescription pad compartment 208 and electrically connected to the alarm system 102 to trigger the alarm speaker 112 if the prescription pad 210 is removed from prescription pad compartment 208 when the alarm system 102 has been enabled.

A reflex hammer compartment 214 is preferably provided for receiving a conventional neurology reflex hammer 216. At least one and preferably two penlight/writing instrument compartments 218 are preferably provided generally opposite each other and adjacent the reflex hammer compartment 214, each for receiving a conventional penlight and/or writing instrument 220. The prescription pad compartment 208, reflex hammer compartment 214, and penlight/writing instrument compartments 218 are preferably arranged on a portion of the portable housing 12 generally opposite to, and having a greater thickness than, the medical device compartment 28 portion of portable housing 12.

A calculator recess 222 is preferably defined in the undersurface 86 of the portable housing 12 for receiving a due-date calculator 224. The recess 222 is preferably coextensive with the housing such that the calculator 224 may be removed from or inserted into the calculator recess 222 on either side of the housing 12 and thus regardless of the orientation of portable housing 12 with respect to examination table 69. A calculator retaining clip 226 or the like made of a metal, plastic, composite, or like resilient material is preferably provided attached to and biased upward toward the portable housing undersurface 86 for retaining the due-date calculator 224 within calculator recess 222 during transport or reorientation of portable housing 12. The calculator retainer clip 226 may also assist in retaining a portion of scan cable 144 as it is entrained along portable housing undersurface 86.

At least one and preferably four chart retaining clips 228 are preferably mounted to the portable housing 12 for retaining a conventional medical chart 230. The chart clips 228 are preferably made of a metal, plastic, composite, or other generally resilient material known to those skilled in the art. A notepad compartment 232 is preferably mounted to free end wall 233 of the portable housing 12 for holding a small paper notepad 234 of writing papers and for dispensing sheets therefrom. The notepad compartment 232 is preferably sized and shaped to retain therein the paper notepad 234.

Referring now to FIGS. 1, 2, 16, and 17, a handle 236 is preferably pivotally attached to the portable housing 12 by pins 238 or the like. The handle is thereby capable of being arranged in a stored position so as not to obstruct access to other components such as the gel container 180, gel bottle compartment 30, or control panel 190, and also pivoted to a generally upright position to facilitate compactly and easily transporting medical devices and supplies accommodated by the portable housing 12.

A lock/release mechanism 240 is preferably provided to eliminate any potential rotational instability of portable housing 12 about pivotal handle 236 as the practitioner 66 carries it or attempts to mount it to base housing 14. The lock/release mechanism 240 automatically locks pivotal handle 236 in the generally upright position when portable housing 12 is disconnected from base housing 14 and releases the handle 236 so that it may rotate by gravity to the stored position when portable housing 12 is connected to base housing 14.

The handle lock/release mechanism 240 preferably comprises at least one locking slot 242 defined in an end 244 of pivotal handle 236 and a locking arm 246 having a first segment 248 with a locking tab 250 extending therefrom and capable of being received by the locking slot 242. The locking arm 246 has a second segment 252 preferably angled with respect to the first segment 248. The second segment 252 has a flange 254 disposed thereabout and a head 256 disposed thereon and generally extending at least partially through an opening 258 defined in the bracket endwall 147 of portable housing 12. The head 256 preferably has a compression surface 259 generally angled with respect to the bracket endwall 147 to provide movement of the locking arm second segment 252 in an axial direction in response to engagement of the head 256 by the base housing 14 in a direction normal to the axis of the locking arm second segment 252. The second segment 252 of locking arm 246 slidingly extends through a sleeve 260 fixedly attached to the portable housing 12, and a spring 262 such as a coil spring or the like is disposed about the second segment 252 generally between sleeve 260 and flange 254. The elasticity of the spring 262 is selected so that the spring 262 acts on the fixed sleeve 260 and the flange 254 of the slidable locking arm second segment 252 to bias the head 256 at least partially through the endwall opening 258 and to bias the locking tab 250 into the locking slot 242 and thereby lock pivotal handle 236 in an upright position when the portable 12 and base 14 housings are not connected. The elasticity of the spring 262 is further selected so that when portable 12 and base 14 housings are connected, the base housing 14 engages and depresses the locking arm head 256 to remove the locking tab 250 from the locking slot 242 and thereby release the pivotal handle 236.

The locking arm 246 preferably has a generally circular cross-section, though it may optionally be provided with a rectangular or other regular or irregular cross-section known to those skilled in the art. The handle 236, locking arm 246, and coil spring 262 are preferably made of a metal, plastic, composite, or other material known to those skilled in the art.

Optional lock/release mechanisms 240 known in the art may be suitably employed. For example, there may be provided a pivotal handle 236 with two locking slots 242 defined in opposite sides thereof and a locking arm 246 with two tabs 250 extending therefrom and oppositely faced so that the handle 236 may be locked in both upright and stored positions. Alternatively, there may be provided a cam assembly so upon disconnection of the portable 12 and base 14 housings, the lock arm 246 is rotated into contact with the handle end 244 until the lock tab 250 is aligned with the locking slot 242 to thereby provide automatic locking of the handle 236 regardless of the position of the handle 236.

Figure 18:
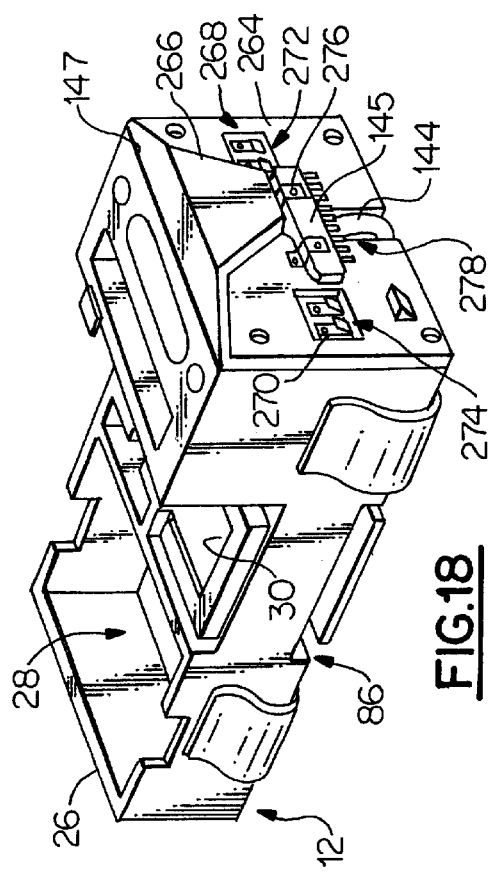
FIG. 18 is a perspective view of the portable housing.

Referring to FIG. 18, the bracket endwall 147 is preferably provided with at least one electrical power supply contact 268 and at least one electrical signal contact 270 arranged thereon. A mounting bracket 264 with a bracket arm 266 extending therefrom is preferably attached to the bracket endwall 147 by screws, nuts and bolts, clamps, an adhesive, or other attachment methods known to those skilled in the art. The mounting bracket 264 is preferably generally flat with at least one and preferably two contact apertures 272 and 274 defined therein, where at least one contact aperture 272 is capable of alignment with the electrical power contact 268 and at least one contact aperture 274 defined therein and capable of alignment with the electrical signal contact 270. The contact apertures 272 and 274 allow the respective contacts 268 and 270 to extend at least partially therethrough.

The scanhead electrical plug 145 is preferably removably attached to the mounting bracket 264 by fasteners 276 such as clamps, clips, screws, nuts and bolts, or other fasteners known to those skilled in the art. A notch 278 may be formed in the bracket 264 generally aligned with the cable channel 1:50 in the portable housing undersurface 86 so that the scanhead cable 144 may be routed therethrough.

It should be noted that the bracket 264 may be provided as a separate removable structure from the portable housing 12 as described hereinabove or it may be integrally formed with the portable housing 12. Where the bracket 264 is integrally formed with the portable housing 12, the electrical power contacts 268 and electrical signal contacts 270 are arranged on the integral endwall bracket.

Figure 19:
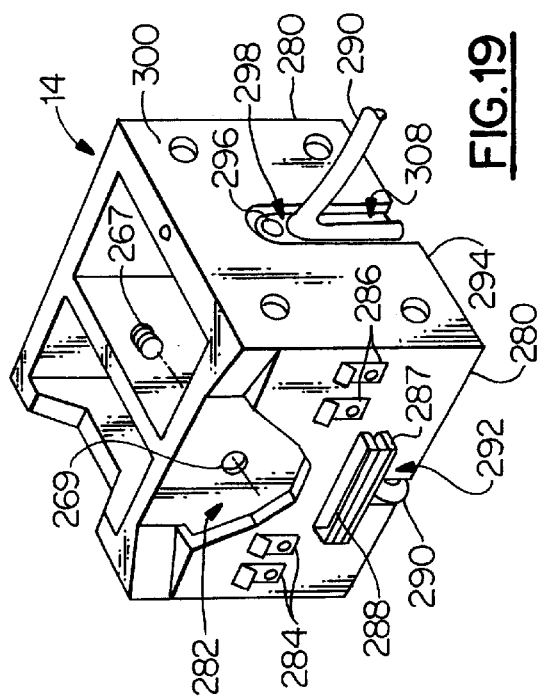
FIG. 19 is a perspective view of a base housing of the present invention.

Referring now to FIG. 19, the base housing 14 preferably has two substantially identical and opposite receptacle endwalls 280, each having a receptacle 282 formed therein with a size and shape to be capable of receiving the bracket arm 266 of the portable housing 12 or of the optional housings 17 described hereinbelow for structural linkage and support thereof. For applications where it is desirable for the portable and base housings 12 and 14 to be connected together for a relatively long time, at least one set screw 267 or the like may be installed through at least one threaded aperture 269 in the endwall 280 to engage the bracket arm 266 to thereby prevent the housings 12 and 14 from disconnecting inadvertently.

The receptacle endwall 280 is preferably provided with at least one electrical power supply contact 284 and at least one electrical signal contact 286 arranged thereon in an arrangement similar to that of bracket endwall 147. The electrical power supply contact 284 is capable of aligning with and electrically connecting with the electrical power supply contact 268 of the portable housing and the electrical signal contact 286 is capable of aligning with and electrically connecting with the corresponding electrical signal contacts 270 of the portable housing.

Preferably, the contacts 268, 270, 284, and 286 are each provided by two angled metal strips fastened to the housings 21 by screws or the like and which are generally oppositely aligned with two metal strips on adjacent housings 21. Optionally, the contacts 268, 270, 284, and 286 may be comprise multi-pin connectors, jacks, plugs, or other electrical connectors known to those skilled in the art and selected for permitting ready attachment and detachment thereof. It should also be noted that the contacts 268, 270, 284, and 286 may be arranged generally vertically, generally horizontally, generally diagonally, or in other regular or irregular arrangements on the housings 21. Finally, the capability of connecting portable housing 12 and/or one of the optional housings 17 to either one of the two opposing receptacle end walls 280, requires that the side-to-side array and polarity of all electrical contacts upon receptacle end wall 280 be duplicated upon the alternate and opposing endwall 280. This may be accomplished by means of a chiasm of connecting wires within the base housing 14, by specialized electical connections, or by other means known to those skilled in the art.

When apparatus 10 is employed in conjunction with sonography, a scanhead electrical receptacle 288 is preferably attached to the endwall 280 by fasteners 287 such as clamps, clips, screws, nuts and bolts, or other fasteners known to those skilled in the art. The scanhead electrical receptacle 288 is capable of aligning with and electrically connecting with the scanhead electrical plug 145 of the portable housing. It should be noted that the scanhead electrical plug 145 and receptacle 288 may be provided by any type of electrical multi-pin connector known to those skilled in the art and selected for permitting ready attachment and detachment thereof. A sonogram connector cable 290 is preferably connected to the electrical receptacle 288 and routed through a cable channel 292 formed in an undersurface 294 of the base housing 14.

The portable housing 12 is thus capable of being structurally and electrically connected to and supported by the base housing 14. To connect the housings 12 and 14, the portable housing endwall 147 is positioned generally above and adjacent to the base housing receptacle endwall 280, thereby generally aligning the portable housing bracket arm 266 and the base housing receptacle 282, generally aligning the respective electrical contacts 268, 270, 284, and 286, and generally aligning the scanhead plug 145 and receptacle 288. The portable housing 12 is then structurally and electrically connected to the base housing 14 by a generally downward motion of the portable housing 12 by the practitioner 66. Conversely, the portable housing 12 may be structurally and electrically disconnected from the base housing 14 by a generally upward motion on the portable housing 12 by the practitioner 66, by means of pivotal handle 236.

Because receptacle endwalls 280 are substantially identical, any of the housings 21 may be mounted to any endwall 280 of the base housing 14. This versatility allows the entire apparatus 10 to be mounted to the opposite side of examination table 69 or in other arrangements. It should be further noted that the base housing 14 may optionally be provided with three or more receptacle endwalls 280 each capable of receiving any of the housings 21. For example, the base housing 14 may be provided with a plan profile that is rectangular, semi-hexagonal, semi-octagonal, or another regular or irregular shape known to those skilled in the art. Conversely, in the simplest optional arrangement, only the portable housing 12 and the table mounting bracket 16 may optionally be employed. The portable housing bracket end wall 147 may be electrically and physically connected to housing end 310 of the bracket 16 by an intervening housing-to-bracket adaptor plate (not shown) having one surface essentially identical to receptacle endwalls 280, and having the opposite surface connecting to housing end 310 of bracket 16, and providing for passage of electrical and sonogram cables and connectors therethrough, to appropriate electrical supply and sonogram console external to apparatus 10.

Figure 20:
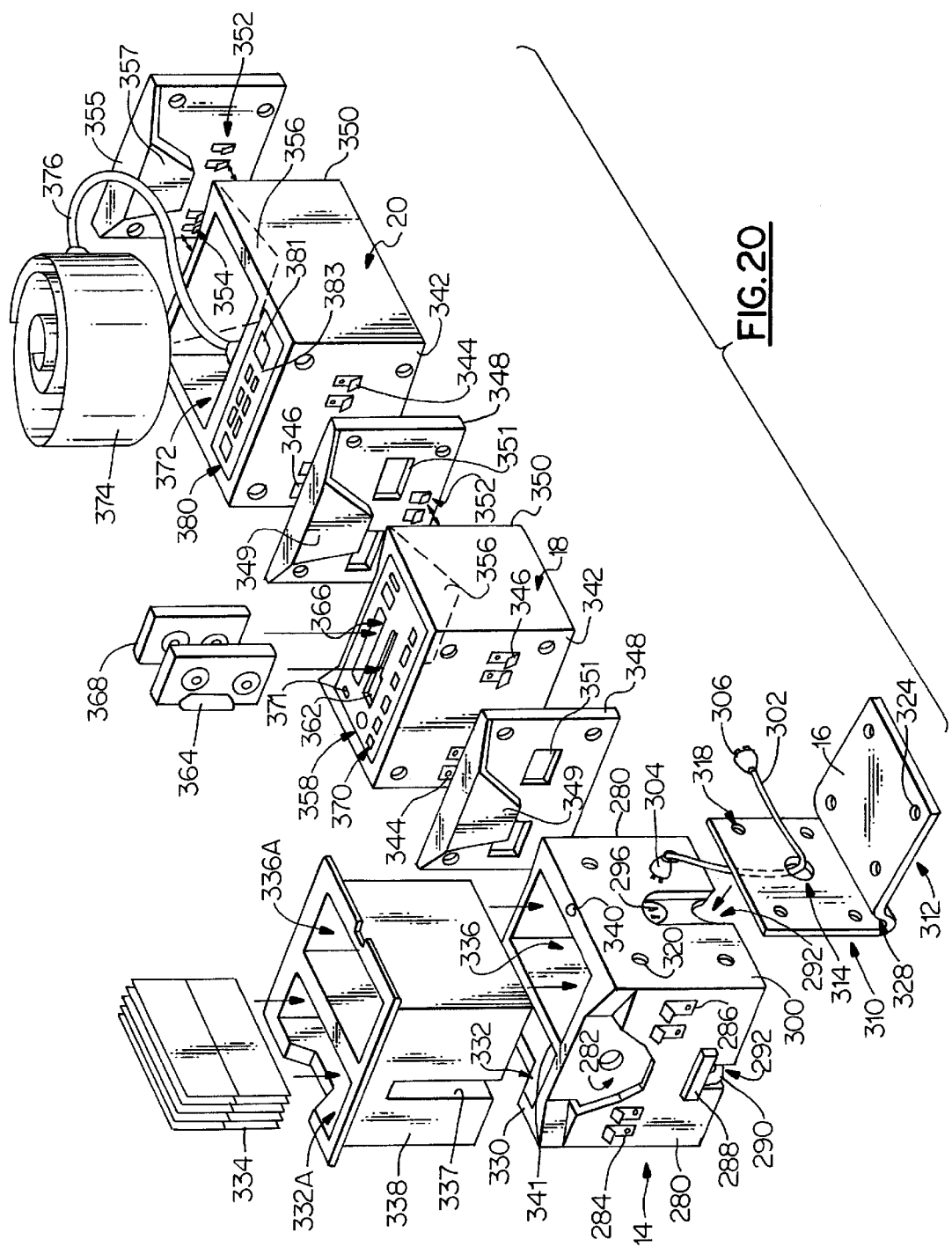
FIG. 20 is an exploded perspective view of the base and optional housings of the present invention, showing several medical implements typically used in conjunction therewith.

Referring now to FIGS. 19 and 20, at least one electric power socket 296 is preferably arranged within at least one socket opening 298 defined in a fixture mounting sidewall 300 of the base housing 14. An electric power cord 302 may be provided having electric plugs 304 and 306 on each end, electric plug 304 capable of being electrically connected to the electric power socket 296 and electric plug 306 capable of being electrically connected to the external power supply 140 described hereinabove.

The fixture mounting sidewall 300 preferably has a cable channel 308 defined therein and in communication with the undersurface cable channel 292 for routing therethrough the sonogram connector cable 290. There may be provided cover plates, clips, hooks, or the like for securing the cable 290 within cable channels 292, 308. There may optionally be provided an additional connector (not shown) in the sonogram connector cable 290, arranged on or within the base housing 14 and preferably within or generally proximate to the electric power socket 296, permitting quick and easy connection and disconnection of the electric power cord 302 and the sonogram connector cable 290 at the fixture mounting sidewall 300 of the base housing 14. It should be noted that the power cord 302 and the sonogram cable 290 may be sheathed together into a combination cable assembly and a single connector may be provided therefor.

The base housing 14 is attached to the examination table 69 by the fixture mounting bracket 16. Weight and other forces such as inherent torque, tensile, and shear stresses generated by the attachment and use of the portable housing 12 and/or the optional housings 17 are supported and withstood by the base housing 14. The fixture mounting bracket 16 is preferably made of a metal, plastic, composite, or other material selected for providing sufficient strength to withstand the above described forces. It may also be preferable to provide strength enhancing features to resist deformation of the base housing 14 and fixture mounting bracket 16 due to such forces. The selection of strength enhancing features is informed by the number, weight, and type of medical devices and supplies used, and the number, weight, and type of optional housings 17 provided. It should be noted that the fixture mounting bracket 16 may be provided for mounting the base housing 14 to another fixture such as a wall, counter, cabinet, or the like as may be desired in a given application, or apparatus 10 may be provided without the fixture bracket 16 in applications where it may be desirable to arrange the base housing 14 on a countertop or the like without anchoring means.

To provide additional strength for the base housing 14, an internal frame (not shown) made of metal, composite, or a like material for strength, is preferably disposed within the base housing 14. Optionally, added strength may be provided by a plate (not shown) attached to base housing undersurface 294, by ribs or like braces on exterior or interior walls, or by other methods known to those skilled in the art.

The fixture mounting bracket 16 preferably has a housing end 310 for attachment to the fixture mounting sidewall 300 of base housing 14, and a table end 312 for attachment to the examination table 69, with the table end 312 at an angle relative to the housing end 310. Housing end 310 preferably has at least one electrical opening 314 defined therein with a portion thereof generally alignable with socket opening 298 and at least a portion of cable channel 308 of fixture mounting sidewall 300 of the base housing 14. The electrical opening 314 is preferably sized to receive therethrough the electric cord 302 with plugs 304 and 306 and/or sonogram connector cable 290. Optionally, the electrical opening 314 may be sized to receive therethrough the electric cord 302 but not the end plugs 304 and 306, with the opening 314 provided as a notch or the like for laterally inserting and/or removing the electric cord 302 therefrom. It should be noted that optionally the mounting bracket 16 may be adapted to directly structurally and electrically connect to and support the portable housing 12, thereby eliminating the base housing 14 from the apparatus 10.

The base housing 14 is preferably mounted to the housing end 310 of the fixture mounting bracket 16 by conventional fasteners such as screws through bracket apertures 318 and threaded housing apertures 320. Optional fasteners that may be suitably employed include bolts, pins, clamps, hooks, adhesives, or other fasteners known to those skilled in the art. The electrical opening 314 and bracket apertures 318 may be generally symmetrically arranged on the housing end 310 of the fixture mounting bracket 16 and the socket opening 298 and threaded housing apertures 320 may be generally symmetrically arranged on the fixture mounting sidewall 300 of the base housing 14. These symmetrical arrangements are preferably such that the base housing 14 may be mounted to the housing end 310 of the bracket 16 with housing end 310 extending either generally downward or generally upward from the table end 312 of the fixture mounting bracket 16.

The table end 312 of the fixture mounting bracket 16 is preferably mounted to the examination table 69 by conventional fasteners such as screws through bracket apertures 324 and threaded table apertures (not shown). Optional fasteners that may be suitably employed include bolts, pins, clamps, hooks, adhesives, or by other fasteners known to those skilled in the art. The table end 312 is preferably attached to a base cabinet (not shown) of the examination table 69 with the housing end 310 extending generally upward from the table end 312 to position the apparatus 10 and the medical devices and supplies stored therein at the approximate height of the supine patient 68 resting upon the cushioned surfaces of examination table 69. To achieve a similar height where apparatus 10 is mounted to an examination table 69 lacking a base cabinet, table end 312 of fixture mounting bracket 16 may be inverted and attached between the top surface (not shown) of the examination table 69 and the table cushion (not shown) which rests thereupon, with the housing end 310 of fixture mounting bracket 16 extending generally downward from the table end 312. Additionally, the fixture mounting bracket 16 preferably has a bracket groove 328 formed therein which can accommodate the cushion retaining rim (not shown) of some examination tables 69.

Referring now to FIG. 20, the base housing 14 preferably has an upper surface 330 with at least one compartment defined therein. Preferably, the base housing 14 has a tissue supply compartment 332 for storing a supply of conventional tissue 334, moist wipes, gauze, or the like, and a waste compartment 336 for disposal of the used tissues (not shown). The waste compartment 336 may optionally be used for storage space for medical supplies of the practitioner's 66 choice, such as a wide blood pressure cuff (not shown) to fit the arms of obese patients 68, earphones (not shown) which accompany certain models of conventional Doppler devices 36, and the like.

A removable insert tray 338 is preferably provided for ease of cleaning and/or for disposal of the used tissue and other waste from these compartments 332 and 336. The tray 338 is preferably made of plastic, paper, cardboard liner or the like so as to itself be disposable. The tray 338 preferably has two compartments 332A and 336A, for tissue supply and waste respectively, separated by two spaced apart divider walls 337 which generally conform to and receive therebetween a divider wall 341 formed between the tissue supply compartment 332 and the tissue waste compartment 336. A notch 339 is preferably defined in the tray 338 for permitting ease of access to the tissue 334 disposed within the tissue compartment 332. Optionally, a single compartment insert tray may be provided for the waste compartment 336A only, two single-compartment insert trays may be provided with one for the tissue supply compartment 332A and another for the tissue waste compartment 336A, or a single compartment may be provided in the base housing 14 for receiving the two-compartment tray 338.

Figure 22:
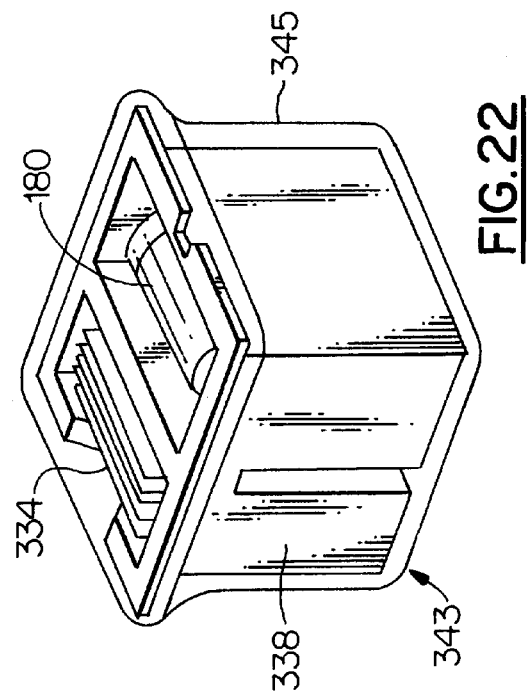
FIGS. 21 and 22 are perspective views of a disposables kit provided by the present invention.
Figure 21:
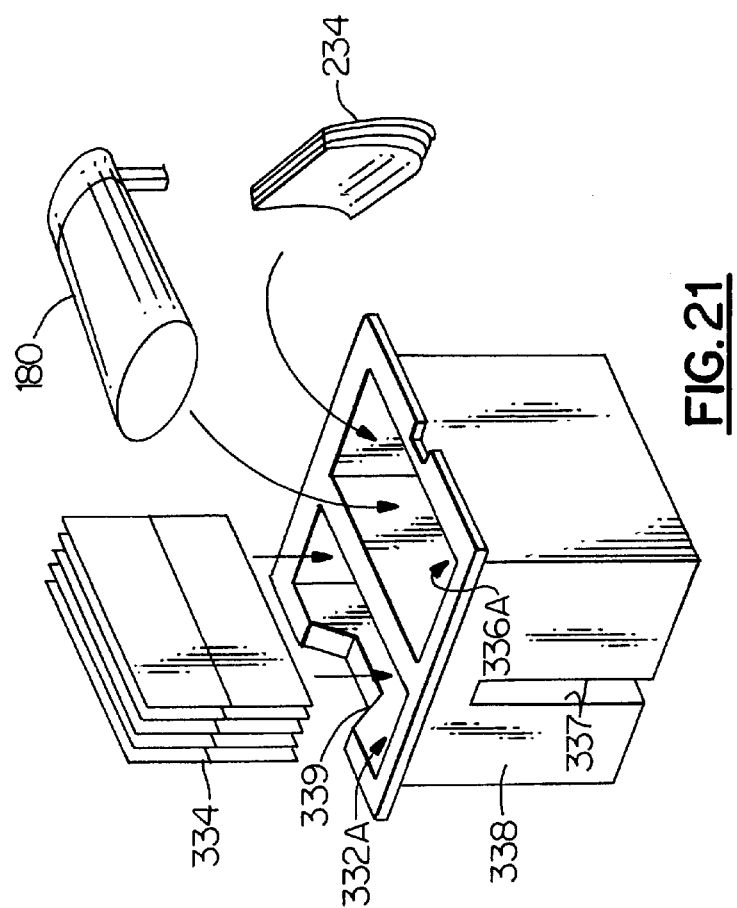

Referring now to FIGS. 21 and 22, a unique feature provided by the present invention is that a disposables kit 343 may be provided to periodically restock apparatus 10. The disposables kit 343 preferably comprises the insert tray 338 with gel container 180, tissue supply 334, paper notepad 234, and/or other medical supply items contained therein and packaged with a wrapping 345 such as plastic, paper, cardboard, or the like, disposed thereabout for shipping. This arrangement is also preferable for providing compactness during shipping, storage, and use of the apparatus 10. Kit 343 optionally can incorporate an additional supply of conventional tissue 334, moist wipes, gauze, or the like; and a second insert tray for disposal of expended supplies; for offices which deplete tissues/wipes/gauze more rapidly than the contents of a single gel container 180.

Referring back to FIG. 20, a power indicator light 340 is preferably provided to indicate power or the lack thereof to the housings 21. The power indicator light 340 preferably comprises a light bulb, light emitting diode, liquid crystal display, or other light emitting device known to those skilled in the art. The power indicator light 340 is preferably mounted on the upper surface 330 of the base housing 14 or at a like generally prominent position for ease of viewing.

Optional housings 17 may be provided for organizing, storing, transporting, and facilitating the use of other medical devices and supplies. The recording housing 18 and the blood pressure housing 20 are described herein, though alternate or additional housings may be provided with storage compartments configured for accommodating other medical equipment and supplies. Such other accommodated equipment and supplies may include laboratory or radiology request forms too large to fit the prescription pad compartment 208, business cards of medical practices to which the practitioner 66 commonly refers patients 68, earphones for privately listening to Doppler sounds, individually wrapped phenaphthazine test swabs, individually wrapped cleansing or antiseptic pads for Doppler probe or sonogram scanhead cleansing, disposable latex vaginal probe covers which are used with the vaginal scanhead, and/or any other items deemed useful in the particular medical setting.

Each of the optional housings 17 preferably has a bracket endwall 342 with at least one electrical power supply contact 344 and at least one electrical signal contact 346 arranged thereon and having a mounting bracket 348 attached thereto with a bracket arm 349 extending therefrom and contact openings 351 defined therein all in a substantially identical arrangement as the contacts 268 and 270 and the mounting bracket 264 of the endwall 147 of the portable housing 12. Each of the optional housings 17 preferably has a receptacle endwall 350 arranged generally opposite of bracket endwall 342 and having at least one electrical power supply contact 352 and at least one electrical signal contact 354 arranged thereon and having a receptacle 356 formed therein in a substantially identical arrangement as the contacts 284 and 286 and the receptacle 282 of either of the receptacle endwalls 280 of the base housing 14. The housings 21 are thus generally interchangeable because any receptacle endwall 280 or 350 and any mounting bracket 264 or 348 may be structurally and electrically connected together.

At least one end cap 355 is preferably provided for removably connecting to and generally covering a receptacle endwall 280 or 350 of any of the housings 14, 17. The endcap 355 is preferably generally flat with a bracket arm 357 extending therefrom, the bracket arm 357 having a substantially identical shape and size as the bracket arms 266 and 349 of the mounting brackets 264 and 348 so as to be capable of removably connecting to any of the receptacle endwalls 280 or 350. The endcap 355 is installed on the receptacle endwall 280 or 350 of the housing 14, 17 situated furthest from the portable housing 12 to protect the contacts; 284, 286, 352, and 354 arranged thereon and to enhance the cosmetic appearance of the apparatus 10. The endcap 355 may optionally be removably attached to the receptacle endwall 280 or 350 by screws, bolts, clips, clamps, adhesives, or other fasteners known to those skilled in the art.

The recording housing 18 is preferably provided with a conventional audio and/or video recorder and/or player 358 for use with Doppler and/or sonography equipment. Preferably, Doppler audio recording functions are provided by an audio recorder/player such as a conventional audio-cassette recorder/player 358. Optionally, real-time sonogram image recording functions, with accompanying doctor-patient dialogue, may be provided by an audio and video recorder/player such as a conventional videocassette recorder/player. It should be noted that the audio/video recorder/player 358 may optionally be provided by conventional audio and/or video recording and/or playback devices such as compact disc, CD-ROM, DVD, Dvdx, and/or other digital and/or analog audio and/or video devices known to those skilled in the art for recording and/or playback of the fetal images and/or sounds generated by sonography and/or Doppler investigation.

The preferred conventional audiocassette recorder/player 358 provides for recording and playback of ambient sounds produced by a Doppler device 36, 38. The audiocassette recorder/player 358 preferably comprises an audiocassette compartment 362 for accepting an in-use audiocassette 364 with tape, an audiocassette storage compartment 366 for accepting a spare audiocassette 368, and a player/recorder control 370 having control knobs or the like mounted on a panel and with conventional electric circuitry for recording, playback, stop, eject, rewind, fist forward, and like functions. The control 370 preferably further comprises an auto-record selector switch 371 mounted on the panel for usage as described below.

The patient 68 may thereby bring her personal audiocassette 364 to the medical appointment and install it in the audiocassette recorder/player before the practitioner 66 employs Doppler device 36, 38 to record the fetal sounds. Subsequently, tape recording, the cessation thereof, and cassette ejection may be automatically managed by auto-record control circuit 385, described hereinafter. The patient 68 may then remove her ejected personal audiocassette 364 from the audiocassette recorder/player at the conclusion of the prenatal visit. When staff has once demonstrated to the patient 68 this use of recording housing 18, she may thenceforth independently obtain a brief keepsake recording from each prenatal visit.

The blood pressure housing 20 is preferably provided having a pressure cuff compartment 372 for receiving a conventional blood pressure cuff 374. The blood pressure cuff 374 is preferably connected to the blood pressure housing 20 by a generally flexible pressure tubing 376 which has a conventional air compression device (not shown) connected thereto for cuff inflation-deflation cycles, and a conventional pressure transducer (not shown) for accurate blood pressure determinations. A blood pressure control 378 (see FIG. 23) is preferably provided having a control panel 380 with a pressure cycle switch 381 and a blood pressure display 383 and having conventional electric circuitry for the electrical operation thereof. Depression of the pressure cycle switch 38 initiates one measurement of systolic, diastolic, and mean arterial blood pressures, which are digitally displayed at the blood pressure display 383.

One such conventional cycled blood pressure monitoring device is provided by Welch-Allyn, Inc of San Diego, Calif. This conventional device may be adapted and arranged as described herein for use within the blood pressure housing 20 of the apparatus 10, thereby positioning the blood pressure housing 20 and its components generally adjacent and at a comparable height to the patient 68 on the examination table 69 in either supine or lateral decubitus position. This at-table arrangement allows for convenient, accurate and repetitive blood pressure determinations of patients 68, and thereby facilitates the prediction, detection, and monitoring of pregnancy related hypertensive disorders.

Figure 23:
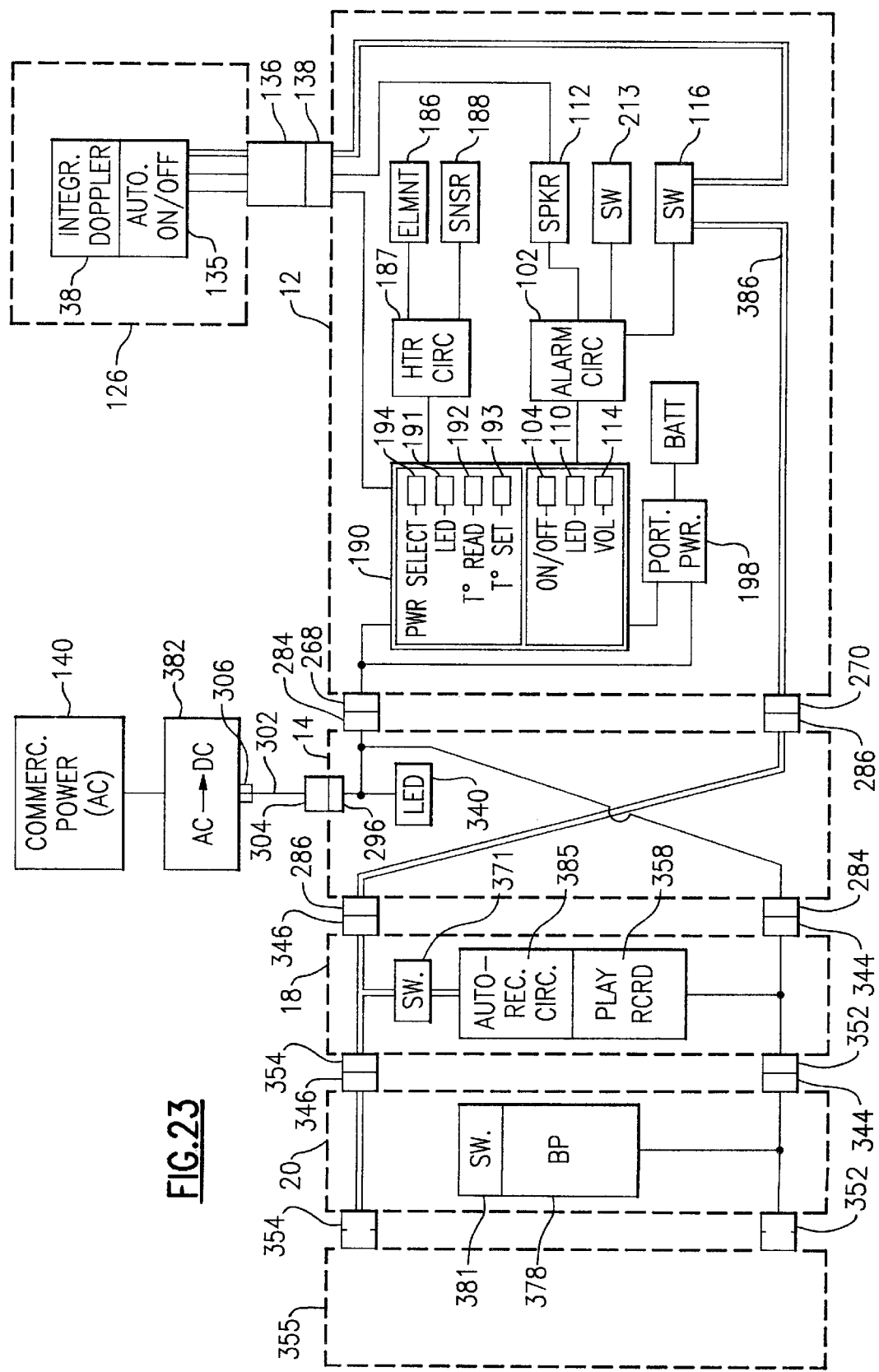
FIG. 23 is a block diagram of the electrical components of the present invention.

Referring now to FIG. 23 and as described hereinabove, where the external power supply 140 is conventional 120/240 VAC, there is preferably provided a conventional AC-DC converter 382 which may be arranged in combination with the electric cord plug 306, for conversion to low-voltage direct current. The power indicator light 340 of base housing 14 is connected to the power cord 302 so as to illuminate when power is connected and available to the apparatus 10.

There is provided at least one electric circuit comprising conventional electrical components known to those skilled in the art for power to and/or control of the apparatus 10 and/or various of the medical devices accommodated thereby. For example, the electric circuits permit operation of gel heater 178, alarm system 102, integral Doppler device 38, optional recording housing 18, and optional blood pressure housing 20.

More specifically, electric power wiring is preferably connected from the external power source 140 and the portable power supply 198 to the control panel 190 and therefrom to the gel heater 187, the alarm system 102, and the integral Doppler device 38 (if optionally employed). Electric power wiring is also preferably connected from the external power source 140 directly to the recording housing 18 and the blood pressure housing 20. Electric control wiring is preferably connected from the control panel 190 by way of gel heater control circuit 187 to the gel heater element 186 and gel temperature sensor 188, and by way of the alarm circuit 102 to contact switches 116 and 213 and the speaker 112, for operation thereof. Controls provided upon panel 190 for gel heater operation preferably include power source selector 194, heater-on indicator light 191, temperature readout 192, and temperature setpoint adjustment 193. Controls provided upon or near panel 190 for alarm system operation include on/off switch 104, system-active LED 110, and volume control 114. Switch 104 and volume control 114 are preferably not located directly upon the control panel 190, for purposes of concealment.

There is preferably provided a circuit for recharging the portable power supply 198 from the external power source 140. All circuits may be accomplished using conventional circuit boards or the like with the conventional electrical components connected thereto. All wiring is preferably internal to the housings 21 for safety and/or is of the insulated type.

There is preferably further provided an auto-record control circuit 385 which comprises the auto-record selector switch 371 described hereinabove for activating/deactivating the control circuit 385, the supply contact 284 and 344 described hereinabove for electrically connecting the recording and base housings 18 and 14, the signal contacts 286 and 346 described hereinabove for electrically connecting the base and recording housings 14 and 18, and electric wiring 386 interconnecting the contact switch 116 of the medical device compartment 28, the signal contacts 284, 286, 344 and 346, and the audio/video recorder/player 358.

The auto-record control circuit 385 is activated by depression of the auto-record selector switch 371. The electric wiring 386 is connected such that when the Doppler primary probe 44, 130 is removed from the probe well 60,128, the contact switch 116 is decompressed which closes the activated circuit 385 and energizes the electric power and control circuitry of the audio/video recorder/player 358 so that it automatically records audio from the Doppler device 36, 38 and ambient conversation from the practitioner 66 and patient 68. When the Doppler in-use probe 44,130 is replaced in the probe well 60,128, the switch 116 is thereby compressed which opens the circuit 385 and automatically discontinues the recording by the audio/video recorder/ player 358 and ejects therefrom the audiocassette 364 or the like. Similarly, video images may be automatically recorded in sonography applications of the apparatus 10. The auto-record control circuit 385 is opened and thereby de-activated by release of the auto-record selector switch 371, so that the audio/video recorder/player 358 functions in conventional fashion.

Referring now to FIG. 24, the mounting bracket 16 is attached to the examination table 69 preferably nearer to the table head 388 than to the table foot 390, to thereby position the apparatus 10 to provide accessibility and ease of use of the obstetric devices and supplies. The practitioner 66 may thus position himself so as to face both the patient 68 and the medical implements and supplies stored in the apparatus 10. The base housing 14 is attached to the mounting bracket 16 to provide a generally fixed location for common supplies and accessories, and to offer interchangeable support locations for the portable housing 12 and the optional housings 17. Electric cord 302 and console connector cable 290 are routed from the base housing 14 through the opening 314 for connection to AC-DC converter 382 and to remote sonogram console 146, respectively.

Many conventional examination tables have a toggle lever 392 at each side of the table head 388 for adjusting the angle of the back support to provide patient 68 comfort. The preferred position of the apparatus 10 may result in the toggle lever 392 being between the table 69 and the apparatus, with hindered access thereto. A toggle extension 394 may be provided for connecting to the toggle lever 392 so that the user's access to operation of lever 392 is enhanced. Preferably, toggle extension 394 protrudes upwardly between apparatus 10 and the exam table 69. Additionally, the various compartments of the housings 21 are provided with sufficient depth and attachment mechanisms described hereinabove to retain the corresponding medical devices and supplies when the table head 388 is adjusted to the upright position.

In the installation and use of the apparatus 10, the mounting bracket 16 and base housing 14 can be attached to either side of the examination table 69, as desired, to accommodate medical staff preferences and the arrangement of medical furniture within the examination room. Because the two opposing receptacle endwalls 280 of the base housing 14 are substantially identical, the bracket endwall 147 of the portable housing 12 can be connected to either. Consequently, regardless of the side of examination table 69 chosen for apparatus 10, the practitioner 66 can always connect portable housing 12 to base housing 14 so that the Doppler device 36, 38 or sonogram scanhead 142 is adjacent both patient 68 and practitioner 66. This arrangement is highly desirable because Doppler base units 42, 125 may have a fetal heart rate readout and this arrangement allows the readout always to be visible to practitioner 66. Additionally, the Doppler probes 44, 130 and the sonogram scanhead 142 are thereby arranged near the patient 68, enabling use of conventional Doppler devices 36 having short base-to-probe wires 46 and permitting use of sonogram scanhead assemblies 40 with a short length of scan cable 144. Furthermore, the Doppler receiving insert 50 can be rotated 180 degrees within medical device compartment 28, providing additional flexibility in locating the probe well 60 so as to situate primary probe 44 immediately adjacent to the patient 68 if the practitioner 66 so elects; or instead the practitioner 66 may use Doppler receiving insert 50 to orient the conventional Doppler device 36 for nearness of its primary probe 44 to the dominant hand of practitioner 66.

The present invention can be advantageously used in a wide variety of arrangements, including with only the portable 10 and base 14 housings or with a number of optional housings 17 providing additional medical devices and supplies. All housings 21 preferably have a similar cross-section at their endwall connections for providing a seamless appearance. The optional recording housing 18 and blood pressure housing 20 connect interchangeably to the base housing 14 and may be coupled to each other and to base housing 10.

The portable housing 12 is a compact portable unit that can be either fixedly or removably attached to either of the receptacle endwalls 280 of the base housing 14. The portable housing 12 conveniently arrays and allows patient-to-patient transport of the Doppler device 36, 38 or of the scanhead assembly 40, the gel heater 178, and other useful medical implements. The portable housing 12 has chart retaining clips 228 for retaining standard medical charts 230 while the apparatus 10 is being hand-carried, thus giving the practitioner 66 a free hand for operating exam room doors or for similar purposes.

The portability of the portable housing 12 affords some security to its contents because it generally accompanies the practitioner 66. Additional security and protection features are provided for the medical devices, including the belt clip pin 96 for receiving a Doppler belt clip 78, the security latch 82 and the guide latch 168, the elastic strap 100, partial concealment provided by the depth of the compartments, and the alarm system 102. Additionally, the gel heater 178 provides adjustable steady-state warming of gels, whether the portable housing 12 is connected to the external power supply 140 through the base housing 14 at tableside or operating on rechargeable battery 198 during transit.

Accordingly, there are a number of advantages provided by the present invention. The present invention provides an apparatus 10 for storing, organizing, transporting, and facilitating the use of medical implements and supplies commonly used during an obstetrical examination, providing the advantage of improved efficiency of the practitioner 66, allowing the performance of more prenatal visits per office day and/or reducing the amount of time spent in performing the existing number of visits.

Another feature provided by the present invention is the lightweight portable housing 12 with compartments adapted for storage of obstetric implements and supplies, with the bracket endwall 147 of portable housing 12 detachable from the receptacle endwall 280 of the base housing 14, to provide portability to housing 12 which permits the practitioner to avoid unnecessary duplication of expensive or misusable obstetric implements in each examination room.

Additional features provided by the present apparatus 10 include a versatile mounting bracket 16 and a mounting sidewall 300 of the base housing 14 for attaching the apparatus 10 to an examination table 69; universal brackets 264, 348 and receptacles 282, 356 for structurally linking and supporting the housings together; a versatile Doppler receiving insert 50 for supporting and securing the conventional Doppler base unit 42; and a versatile scanhead receiving insert 158 for supporting sonogram scanhead assembly 40. These features, particularly when taken together, provide the advantage of adaptability of the apparatus 10 to a wide variety of examination tables 69, conventional 36 and integral 38 Doppler devices, sonogram scanhead assemblies 40, exam room layouts, and practitioner 66 preferences.

Security and protection features provided by the apparatus 10 include compartments for at least partially concealing expensive or otherwise theft-prone devices from the view of persons other than office staff; security latches 82, guide latches 168, magnetic/adhesive strips 98, elastic straps 100, and belt clip pins 96 for securing conventional Doppler base units 42; and pressure sensitive contact switches 116, 213, for activating the alarm system 102 upon removal of the primary Doppler probe 44, 130, conventional Doppler base unit 42, sonogram scanhead 142, or prescription pad 210. These features provide the advantages of a longer useful life of such implements resulting from less frequent tampering, breakage, and theft, and help prevent the forging of narcotic prescriptions.

An additional feature provided by the apparatus 10 is a gel heater 178 with a control panel 190 and a rechargeable power supply 198, providing the advantage of continual warming and temperature maintenance of medical gels, whether the portable housing 12 is attached at the examination table 69 or in transit.

Yet another feature provided by the present invention is the base housing 14 capable of being mounted to the examination table 69 in a variety of arrangements by a mounting bracket 16 and having compartments for convenient storage of and access to medical supplies typically used in every examination room such as tissue, the portable housing 12 removably attachable to either side of the base housing 14 and capable of receiving any conventional Doppler device 36, 38 or scanhead assembly 40 and having the gel heater 178, and where optional housings 17 such as recording 18 and/or blood pressure 20 housings may be removably and interchangeably connected to the base housing 14 and/or to each other. Such versatility provides the advantage of having the implements and supplies consistently organized and accessible in all potential spatial configurations of apparatus 10, such that the attention of the practitioner 66 can be focused on the needs of the patient 68 rather than on the accessibility and management of the implements and supplies.

While the invention has been described in connection with certain preferred embodiments, it is not intended to limit the scope of the invention to the particular forms set forth, but, on the contrary, it is intended to cover such alternatives, modifications, and equivalents as may be included within the true spirit and scope of the invention as defined by the appended claims.

Claimed is:

1. An apparatus for organizing, transporting and facilitating the use of medical devices and supplies such as a Doppler device, a sonogram device, or a gel bottle, the apparatus comprising:
   a) at least one portable housing having at least one mounting bracket associated therewith;
   b) at least one medical device compartment formed in said portable housing;
   c) at least one base housing having at least one mounting receptacle defined thereon that removably couples with said mounting bracket of said portable housing; and,
   d) at least one fixture mounting bracket associated with said base housing,
   wherein said fixture mounting bracket removably attaches to a fixture, said portable housing removably couples with and is supported by said base housing, and said medical device compartment removably receives at least one of said medical devices and supplies.

2. The apparatus of claim 1, further comprising an alarm system having at least one alarm trigger associated with said medical device compartment, wherein said alarm system is capable of being electrically connected to a power supply.

3. The apparatus of claim 2, further comprising a Doppler receiving insert arranged generally within said medical device compartment and generally adjacent to said alarm trigger device, said insert having a mounting shelf, wherein said shelf removably receives said Doppler device.

4. The apparatus of claim 2, further comprising a scanhead receiving insert arranged generally within said medical device compartment and generally adjacent to said alarm trigger device, said insert having an upper plate, wherein said upper plate removably receives a sonogram scanhead of said sonogram device.

5. The apparatus of claim 4, wherein said portable housing has at least one sonogram electrical connector associated therewith and said base housing has at least one sonogram electrical connector associated therewith that removably connects to said at least one portable housing sonogram electrical connector, wherein said at least one portable housing sonogram electrical connector is electrically connected to a sonogram scanhead and said at least one base housing sonogram electrical connector is electrically connected to a sonogram console.

6. The apparatus of claim 1, further comprising an integral Doppler device comprising a base unit arranged generally within and coupled to said medical device compartment, at least one probe coupled to said base unit, at least one probe well defined in said base unit for receiving said probe, and at least one electric plug extending from said base unit, wherein said medical device compartment has an electric receptacle arranged therein that removably receives and electrically connects to said electric plug, and wherein said electric receptacle is capable of electrically connecting to a power supply.

7. The apparatus of claim 1, further comprising at least one portable power supply associated with said portable housing.

8. The apparatus of claim 1, wherein said portable housing has at least one electric contact and said base housing has at least one electric contact that is removably connectable to said at least one portable housing electric contact, wherein said at least one base housing contact is capable of being electrically connected to an external power supply.

9. The apparatus of claim 1, further comprising a gel bottle compartment formed in said portable housing, wherein said gel bottle compartment removably receives said gel bottle.

10. The apparatus of claim 9, wherein said gel bottle compartment further comprises a gel heater arranged generally within said gel bottle compartment, wherein said gel heater is capable of being electrically connected to a power supply.

11. The apparatus of claim 10, further comprising a heater control electrically connected to said gel heater and having at least one temperature sensor positioned generally proximate to said gel heater and having a control panel with at least one temperature readout and at least one temperature set-point control.

12. The apparatus of claim 1, further comprising at least one additional compartment formed in said portable housing, said additional compartment selected from the group consisting of a tape measure compartment, a pH test tape compartment, a prescription pad compartment, and a reflex hammer compartment.

13. The apparatus of claim 1, further comprising at least one calculator recess, at least one chart retaining clip, or at least one note pad compartment associated with said portable housing.

14. The apparatus of claim 1, further comprising a carrying handle associated with said portable housing.

15. The apparatus of claim 1, further comprising an automatic lock/release mechanism associated with said carrying handle, wherein said lock/release mechanism prevents movement of said handle from an upright position upon decoupling of said portable housing from said base housing.

16. The apparatus of claim 1, wherein said base housing has at least one compartment formed therein.

17. The apparatus of claim 16, wherein said at least one compartment comprises a tissue supply compartment or a waste compartment.

18. The apparatus of claim 1, further comprising at least one optional housing having at least one mounting bracket associated therewith that removably couples with said receptacle of said base housing, at least one mounting receptacle defined thereon, and at least two electric contacts arranged thereon with at least one of said contacts removably connectable to said at least one base housing electric contact.

19. The apparatus of claim 18, wherein said at least one optional housing comprises a recording housing having an audio/video player/recorder, wherein said at least one optional housing electric contact and said at least one base housing contact are removably connectable for electrically connecting said audio/video player/recorder to said Doppler device or said sonogram device.

20. The apparatus of claim 19, further comprising an auto-record system comprising an auto-record selector switch, at least one trigger device arranged generally within said medical device compartment, and signal contacts associated with said recording housing, said base housing, and said portable housing that electrically connect said selector switch and said trigger, wherein said auto-record system is capable of being electrically connected to a power supply.

21. The apparatus of claim 18, wherein said at least one optional housing comprises a blood pressure housing having a blood pressure cuff compartment formed therein and a blood pressure control, wherein said compartment removably receives a blood pressure cuff and said control operates said cuff.

22. An apparatus for organizing, transporting and facilitating the use of medical devices and supplies such as a Doppler device, a sonogram device, or a gel bottle, the apparatus comprising:
   a) at least one portable housing;
   b) at least one medical device compartment formed in said portable housing;
   c) at least one gel bottle compartment formed in said portable housing; and
   d) at least one alarm system having at least one trigger device arranged generally within said medical device compartment,
wherein said medical device compartment removably receives at least one of said medical devices and supplies, said gel bottle compartment removably receives said gel bottle, and said alarm system is capable of being electrically connected to a power supply.

23. The apparatus of claim 22, further comprising a Doppler receiving insert arranged generally within said medical device compartment and generally adjacent to said alarm trigger device, said insert having a mounting shelf, wherein said shelf removably receives said Doppler device.

24. The apparatus of claim 23, wherein said Doppler receiving insert comprises a divider panel extending from said shelf and a bottom plate extending from said divider panel, said divider panel and said bottom plate cooperating with sidewalls of said medical device compartment to form a primary probe well and said shelf and said divider cooperating with said sidewalls of said medical device compartment to form a standby probe keep, wherein said primary probe well removably receives a primary probe of said Doppler device, said standby probe keep removably receives a standby probe of said Doppler device, and said shelf is capable of supporting said Doppler base unit.

25. The apparatus of claim 23, wherein said trigger device comprises two pressure sensitive contact switches generally symmetrically arranged on generally opposite ends of said bottom wall of said portable compartment so that said bottom plate of said Doppler receiving insert may engage one of said switches when said insert is arranged in a first position and may engage another of said switches when said insert is arranged in a second position at 180 degrees relative to said first position.

26. The apparatus of claim 23, wherein said alarm system further comprises a sensitivity adjustment mechanism having an adjustment post extending generally downward from said insert and a control rod capable of being generally telescopically extended and retracted relative to said adjustment post, said control rod having a head capable of being supported by a bottom wall of said medical device compartment and accessible through at least one sensitivity control aperture defined in said bottom wall.

27. The apparatus of claim 23, further comprising at least one electric plug extending from said integral base unit and at least one electric receptacle arranged in said medical device compartment and removably connectable to said electric plug, wherein said electric receptacle is capable of electrically connecting to a power supply.

28. The apparatus of claim 23, wherein said at least one probe well extends through said integral Doppler base unit and is generally aligned with said at least one contact switch in said medical device compartment.

29. The apparatus of claim 23, wherein said Doppler receiving insert comprises at least one attachment mechanism capable of removably securing said Doppler base unit to said shelf.

30. The apparatus of claim 23, wherein said Doppler receiving insert comprises at least one security arm with at least one security latch extending therefrom that is capable of elastic deformation, and wherein said medical device compartment has at least one aperture defined in a bottom wall thereof that is capable of removably receiving said security latch.

31. The apparatus of claim 30, wherein said Doppler receiving insert comprises two security latches and two apertures generally symmetrically arranged to permit said insert to be removably secured within said medical device compartment in a first position and in a second position that is at 180 degrees relative to said first position.

32. The apparatus of claim 22, further comprising an integral Doppler device comprising a base unit arranged generally within and coupled to said medical device compartment, at least one probe coupled to said base unit, and at least one probe well defined in said base unit that removably receives said probe.

33. The apparatus of claim 22, further comprising a scanhead receiving insert arranged generally within said medical device compartment and generally adjacent to said alarm trigger device, said insert having an upper plate, wherein said upper plate removably receives a sonogram scanhead of said sonogram device.

34. The apparatus of claim 33, wherein said scanhead receiving insert comprises said upper plate with a recess defined therein and a cable notch defined therein, wherein said recess removably receives said scanhead and said cable is capable of extending through said notch.

35. The apparatus of claim 33, wherein said scanhead receiving insert comprises at least one guide arm extending from said upper plate with at least one guide latch extending therefrom and capable of elastic deformation, and wherein said medical device compartment has at least one aperture defined in a bottom wall thereof and capable of removably receiving said guide latch.

36. The apparatus of claim 33, wherein said scanhead receiving insert comprises at least one spring extending from said upper plate and generally adjacent said bottom wall of said medical device compartment to bias said insert generally upward.

37. The apparatus of claim 33, wherein said trigger device comprises two pressure sensitive contact switches generally symmetrically arranged on generally opposite ends of said bottom wall of said portable compartment so that at least one contact surface of said upper plate of said scanhead receiving insert may engage at least one of said switches when said insert is arranged within said medical device compartment.

38. The apparatus of claim 22, wherein said medical device compartment has a bottom wall with at least two apertures defined therein so as to be capable of removably receiving at least one security latch of a Doppler receiving insert or capable of removably receiving at least one guide latch of a scanhead receiving insert.

39. The apparatus of claim 22, further comprising at least one portable power supply associated with said portable housing and capable of being electrically connected to said alarm system, a gel heater, or an integral Doppler device.

40. The apparatus of claim 39, further comprising a control panel having a power source selector electrically connected to said portable power supply, wherein said power source selector is capable of being electrically connected to an external power supply.

41. The apparatus of claim 22, wherein said alarm system further comprises at least one alarm control electrically connected to said trigger device, said alarm control having a speaker, a volume control, and an on/off switch.

42. The apparatus of claim 22, wherein said gel bottle compartment further comprises a gel heater arranged generally within said gel bottle compartment, wherein said gel heater is capable of being electrically connected to a power supply.

43. The apparatus of claim 42, further comprising a heater control electrically connected to said gel heater and having at least one temperature sensor positioned generally proximate to said gel heater and having a control panel with at least one temperature readout and at least one temperature set-point control.

44. The apparatus of claim 22, further comprising at least one additional compartment formed in said portable housing, said additional compartment selected from the group consisting of a tape measure compartment, a pH test tape compartment, a prescription pad compartment, and a reflex hammer compartment.

45. The apparatus of claim 22, further comprising at least one calculator recess, at least one chart retaining clip, or at least one note pad compartment associated with said portable housing.

46. The apparatus of claim 22, further comprising a base housing having at least one mounting receptacle defined thereon that removably couples with a mounting bracket of said portable housing, and having at least one electric contact associated therewith that is electrically connectable with at least one electric contact associated with said portable housing, wherein said portable housing removably couples with and is supported by said base housing.

47. The apparatus of claim 22, further comprising a fixture mounting bracket associated with said base housing, wherein said fixture mounting bracket removably attaches to a fixture.

48. An apparatus for organizing, transporting and facilitating the use of medical devices and supplies such as a Doppler device, a sonogram device, or a gel bottle, the apparatus comprising:

a) at least one portable housing having at least one mounting bracket and at least one electric contact associated therewith;

b) at least one medical device compartment formed in said portable housing;

c) at least one gel bottle compartment formed in said portable housing, said gel bottle compartment having at least one gel heater arranged generally therewithin and at least one heater control electrically connected to said gel heater, said heater control having at least one temperature sensor arranged generally proximate to said gel heater, at least one temperature readout, and at least one temperature setpoint control;

d) at least one alarm system having at least one trigger device arranged generally within said medical device compartment and at least one alarm control electrically connected to said trigger device, said alarm control having a speaker, a volume control, and an on/off switch;

e) at least one portable power supply associated with said portable housing and electrically connectable to said alarm system and said gel heater;

f) at least one control panel with said temperature readout, said temperature setpoint control, and said volume control arranged thereon, and having a power source selector electrically connected to said portable power supply;

g) at least one carrying handle associated with said portable housing, said handle having an automatic lock/release mechanism;

h) at least one base housing having at least one mounting receptacle defined thereon that removably couples with said mounting bracket of said portable housing and having at least one electric contact that is removably connectable to said at least one portable housing electric contact, said base housing having at least one tissue supply compartment or a waste compartment formed therein; and, i) at least one fixture mounting bracket associated with said base housing, wherein said fixture mounting bracket removably attaches to a fixture, said portable housing removably couples with and is supported by said base housing, said lock/release mechanism prevents movement of said handle from an upright position upon decoupling of said portable housing from said base housing, said medical device compartment removably receives at least one of said medical devices and supplies, said gel bottle compartment removably receives said gel bottle, and said alarm system and said gel heater are electrically connected to said power source selector which is electrically connected to said portable housing contacts which are electrically connectable to said base housing contacts which are capable of being electrically connected to an external power supply.

49. The apparatus of claim 48, further comprising a Doppler receiving insert arranged generally within said medical device compartment and generally adjacent to said alarm trigger device, said insert having a mounting shelf, wherein said shelf removably receives said Doppler device.

50. The apparatus of claim 48, further comprising an integral Doppler device comprising a base unit arranged generally within and coupled to said medical device compartment, at least one probe coupled to said base unit, at least one probe well defined in said base unit for receiving said probe, and at least one electric plug extending from said base unit, wherein said medical device compartment has an electric receptacle arranged therein that removably receives and electrically connects to said electric plug, and wherein said electric receptacle is capable of electrically connecting to a power supply.

51. The apparatus of claim 48, further comprising a scanhead receiving insert arranged generally within said medical device compartment and generally adjacent to said alarm trigger device, said insert having an upper plate, wherein said upper plate removably receives a sonogram scanhead of said sonogram device.

52. The apparatus of claim 48, further comprising at least one additional compartment formed in said portable housing, said additional compartment selected from the group consisting of a tape measure compartment, a pH test tape compartment, a prescription pad compartment, and a reflex hammer compartment.

53. The apparatus of claim 52, wherein said on/off switch of said alarm system is arranged generally within one of said additional compartments of said portable housing.

54. The apparatus of claim 52, wherein said additional compartments comprise at least one prescription pad compartment with a spring-biased vertical slide member associated therewith, wherein said compartment removably receives and said slide member slidingly supports said at least one prescription pad.

55. The apparatus of claim 48, further comprising at least one optional housing having at least one mounting bracket associated therewith that removably couples with said receptacle of said base housing, at least one mounting receptacle defined thereon, and at least two electric contacts arranged thereon with at least one of said contacts removably connectable to said at least one base housing electric contact.

56. The apparatus of claim 55, wherein said at least one optional housing comprises a recording housing having an audio/video player/recorder, wherein said at least one optional housing electric contact and said at least one base housing contact are removably connectable for electrically connecting said audio/video player/recorder to said Doppler device or said sonogram device.

57. The apparatus of claim 55, wherein said at least one optional housing comprises a blood pressure housing having a blood pressure cuff compartment formed therein and a blood pressure control, wherein said compartment removably receives a blood pressure cuff and said control operates said cuff.

58. The apparatus of claim 48, further comprising at least one endcap removably received by said receptacle of said base housing or said receptacle of said optional housing.

\* \* \* \* \*